US007381794B2

(12) United States Patent
Moore et al.

(10) Patent No.: US 7,381,794 B2
(45) Date of Patent: Jun. 3, 2008

(54) DIMERIC FUSION PROTEINS AND MATERIALS AND METHODS FOR PRODUCING THEM

(75) Inventors: Margaret D. Moore, Seattle, WA (US); Brian A. Fox, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 347 days.

(21) Appl. No.: 11/075,351

(22) Filed: Mar. 8, 2005

(65) Prior Publication Data

US 2005/0260716 A1 Nov. 24, 2005

Related U.S. Application Data

(60) Provisional application No. 60/551,174, filed on Mar. 8, 2004.

(51) Int. Cl.
*C07K 14/705* (2006.01)
*C07K 16/00* (2006.01)

(52) U.S. Cl. .................................... 530/350; 530/387.1

(58) Field of Classification Search ..................... None
See application file for complete search history.

(56) References Cited

U.S. PATENT DOCUMENTS

| | | | | |
|---|---|---|---|---|
| 5,073,627 | A * | 12/1991 | Curtis et al. | 530/351 |
| 5,447,851 | A | 9/1995 | Beutler et al. | 435/69.7 |
| 5,731,168 | A | 3/1998 | Carter et al. | 435/69.1 |
| 5,837,821 | A | 11/1998 | Wu | 530/387.3 |
| 6,018,026 | A * | 1/2000 | Sledziewski et al. | 530/350 |
| 6,642,356 | B1 | 11/2003 | Humphreys | 530/327 |
| 2002/0103345 | A1 | 8/2002 | Zhu | 530/388.15 |
| 2003/0109000 | A1 | 6/2003 | Moore et al. | 435/69.1 |
| 2004/0086908 | A1 | 5/2004 | Chandrasekher et al. | 435/6 |
| 2004/0138417 | A1 | 7/2004 | Fitzpatrick et al. | 530/350 |

FOREIGN PATENT DOCUMENTS

| | | |
|---|---|---|
| WO | 02/002781 | 1/2002 |
| WO | 03/010202 | 2/2003 |

OTHER PUBLICATIONS

Simmons et al., *Journal of Immunological Methods 263*:133-147, 2002.
Schoonjans et al., *Bioseparation 9*:179-183, 2000.
Schoonjans et al., *The Journal of Immunology 165*:7050-7057, 2000.
Landolfi et al., *The Journal of Immunology 166*:1748-1754, 2001.
Zuo et al., *Protein Engineering 13*(5):361-367, 2000.
Lu et al., *Journal of Immunological Methods 267*:213-226, 2002.
Carter et al., *Current Opinion in Biotechnology 8*:449-454, 1997.
Williams et al., *Ann. Rev. Immunol.* 6:381-405, 1988.
Ashkenazi et al., *Cuurent Opinion in Immunology 9*:195-200, 1997.
Lee et al., *Molecular Biology of the Cell 10*:2209-2219, 1999.
Pantoliano et al., *Biochemistry 30*(42):10117-10125, 1991.
Bodmer et al., *Trends in Biochemical Sciences 27*(1):19-26, 2002.
Hu et al., *Cancer Research 56*:3055-3061, 1996.
Gascoigne et al., *Proc. Natl. Acad. Sci. USA 84*:2936-2940, 1987.
Brekke et al., *Immunology Today 16*(2):85-89, 1995.

* cited by examiner

*Primary Examiner*—Prema Mertz
(74) *Attorney, Agent, or Firm*—Gary E. Parker; Nicholas V. Sherbina

(57) ABSTRACT

Polypeptide fusions, dimeric fusion proteins, and materials and methods for making them are disclosed. One of the polypeptide fusions consists of a non-immunoglobulin polypeptide, a polypeptide linker, a dimerizing domain, and, optionally, a linking polypeptide. Another of the polypeptide fusions consists of a non-immunoglobulin polypeptide, a polypeptide linker, and a second dimerizing domain.

24 Claims, 5 Drawing Sheets

118 ... 125
Ala Ser Thr Lys Gly Pro Ser Val
|CH1 ->

140
Phe Pro Leu Ala Pro Ser Ser Lys Ser Thr Ser Gly Gly Thr Ala

155
Ala Leu Gly Cys Leu Val Lys Asp Tyr Phe Pro Glu Pro Val Thr

170
Val Ser Trp Asn Ser Gly Ala Leu Thr Ser Gly Val His Thr Phe

185
Pro Ala Val Leu Gln Ser Ser Gly Leu Tyr Ser Leu Ser Ser Val

200
Val Thr Val Pro Ser Ser Ser Leu Gly Thr Gln Thr Tyr Ile Cys

215
Asn Val Asn His Lys Pro Ser Asn Thr Lys Val Asp Lys Lys Val
<- CH1|

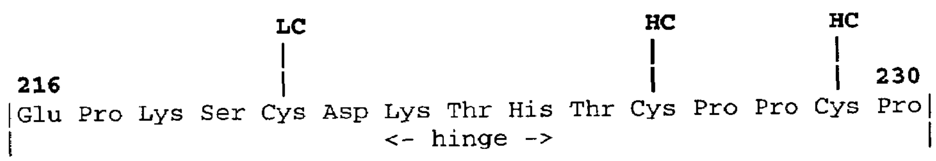

245
|Ala Pro Glu Leu Leu Gly Gly Pro Ser Val Phe Leu Phe Pro Pro
|CH2 ->

260
Lys Pro Lys Asp Thr Leu Met Ile Ser Arg Thr Pro Glu Val Thr

275
Cys Val Val Val Asp Val Ser His Glu Asp Pro Glu Val Lys Phe

290
Asn Trp Tyr Val Asp Gly Val Glu Val His Asn Ala Lys Thr Lys

305
Pro Arg Glu Glu Gln Tyr Asn Ser Thr Tyr Arg Val Val Ser Val

Fig. 1A

```
                                                        320
Leu Thr Val Leu His Gln Asp Trp Leu Asn Gly Lys Glu Tyr Lys

                                                        335
Cys Lys Val Ser Asn Lys Ala Leu Pro Ala Pro Ile Glu Lys Thr

                                                        350
Ile Ser Lys Ala Lys|Gly Gln Pro Arg Glu Pro Gln Val Tyr Thr
                <- CH2|CH3 ->

                                                        365
Leu Pro Pro Ser Arg Asp Glu Leu Thr Lys Asn Gln Val Ser Leu

                                                        380
Thr Cys Leu Val Lys Gly Phe Tyr Pro Ser Asp Ile Ala Val Glu

                                                        395
Trp Glu Ser Asn Gly Gln Pro Glu Asn Asn Tyr Lys Thr Thr Pro

                                                        410
Pro Val Leu Asp Ser Asp Gly Ser Phe Phe Leu Tyr Ser Lys Leu

                                                        425
Thr Val Asp Lys Ser Arg Trp Gln Gln Gly Asn Val Phe Ser Cys

                                                        440
Ser Val Met His Glu Ala Leu His Asn His Tyr Thr Gln Lys Ser

Leu Ser Leu Ser Pro Gly Lys  (SEQ ID NO:1)
```

Fig. 1B

```
gamma1 (SEQ ID NO:48):    Ala Ser Thr Lys Gly Pro Ser Val Phe Pro Leu Ala Pro Ser --- ---
gamma2 (SEQ ID NO:49):    Ala Ser Thr Lys Gly Pro Ser Val Phe Pro Leu Ala Pro Cys --- ---
gamma3 (SEQ ID NO:50):    Ala Ser Thr Lys Gly Pro Ser Val Phe Pro Leu Ala Pro Cys --- ---
gamma4 (SEQ ID NO:51):    Ala Ser Thr Lys Gly Pro Ser Val Phe Pro Leu Ala Pro Cys --- ---
alpha1 (SEQ ID NO:52):    Ala Ser Pro Thr Ser Pro Lys Val Phe Pro Leu Ser Leu Cys --- ---
alpha2 (SEQ ID NO:53):    Ala Ser Pro Thr Ser Pro Lys Val Phe Pro Leu Ser Leu Asp --- ---
delta (SEQ ID NO:54):     Ala Pro Thr Lys Ala Pro Asp Val Phe Pro Ile Ile Ser Gly Cys ---
epsilon (SEQ ID NO:55):   Ala Ser Thr Gln Ser Pro Ser Val Phe Pro Leu Thr Arg Cys Cys Lys
mu (SEQ ID NO:56):        Gly Ser Ala Ser Ala Pro Thr Leu Phe Pro Leu Val Ser Cys --- Glu
consensus (SEQ ID NO:57): Ala Ser Thr Lys Gly Pro Ser Val Phe Pro Leu Ala Pro Cys --- ---

Ser Lys Ser Thr Ser Gly Gly Thr Ala Ala Leu Gly Cys Leu Val Lys Asp Tyr Phe Pro Glu ---
Ser Arg Ser Thr Ser Glu Ser Thr Ala Ala Leu Gly Cys Leu Val Lys Asp Tyr Phe Pro Glu ---
Ser Arg Ser Thr Ser Gly Gly Thr Ala Ala Leu Gly Cys Leu Val Lys Asp Tyr Phe Pro Glu ---
Ser Arg Ser Thr Ser Glu Ser Thr Ala Ala Leu Gly Cys Leu Val Lys Asp Tyr Phe Pro Glu ---
Ser --- Thr Gln Pro Asp Gly Asn Val Val Ile Ala Cys Leu Val Gln Gly Phe Phe Pro Gln Glu
Ser --- Thr Pro Gln Asp Gly Asn Val Val Val Ala Cys Leu Val Gln Gly Phe Phe Pro Gln Glu
Arg His Pro Lys Asp Asn Ser Pro Val Val Leu Ala Cys Leu Ile Thr Gly Tyr His Pro Thr ---
Asn Ile Pro Ser Asn Ala Thr Ser Val Thr Leu Gly Cys Leu Ala Thr Gly Tyr Phe Pro Glu ---
Asn Ser Pro Ser Asp Thr Ser Ser Val Ala Val Gly Cys Leu Ala Gln Asp Phe Leu Pro Asp ---
Ser Arg Ser Thr Ser Gly Gly Thr Val Ala Leu Gly Cys Leu Val Lys Asp Tyr Phe Pro Glu ---

Pro Val Thr Val Ser Trp Asn Ser --- --- Gly Ala Leu Thr Ser Gly Val His Thr Phe Pro Ala
Pro Val Thr Val Ser Trp Asn Ser --- --- Gly Ala Leu Thr Ser Gly Val His Thr Phe Pro Ala
Pro Val Thr Val Ser Trp Asn Ser --- --- Gly Ala Leu Thr Ser Gly Val His Thr Phe Pro Ala
Pro Val Thr Val Ser Trp Asn Ser --- --- Gly Ala Leu Thr Ser Gly Val His Thr Phe Pro Ala
Pro Leu Ser Val Thr Trp Ser Glu Ser Gly Gln Gly Val Thr Ala Arg Asn Phe Pro Pro Ser Gln
Pro Leu Ser Val Thr Trp Ser Glu Ser Gly Gln Asn Val Thr Ala Arg Asn Phe Pro Pro Ser Gln
Ser Val Thr Val Thr Trp Tyr Met Gly Thr Gln Ser Gln Pro Gln Arg Thr Phe Pro Glu Ile Gln
Pro Val Met Val Thr Trp Asp Thr Gly Ser Leu Asn Gly Thr Thr Met Thr Leu Pro Ala Thr Thr
Ser Ile Thr Phe Ser Trp Lys Tyr Lys Asn Asn Ser Asp Ile Ser Ser Thr Arg Gly Phe Pro Ser
Pro Val Thr Val Ser Trp Asn Ser --- --- Gly Ala Leu Thr Ser Gly Val His Thr Phe Pro Ala
```

Fig. 2A

```
Val Leu Gln Ser --- Ser Gly Leu Tyr Ser Leu Ser Ser Val Val Thr Val Pro Ser Ser Ser Leu
Val Leu Gln Ser --- Ser Gly Leu Tyr Ser Leu Ser Ser Val Val Thr Val Pro Ser Ser Asn Phe
Val Leu Gln Ser --- Ser Gly Leu Tyr Ser Leu Ser Ser Val Val Thr Val Pro Ser Ser Ser Leu
Val Leu Gln Ser --- Ser Gly Leu Tyr Ser Leu Ser Ser Val Val Thr Val Pro Ser Ser Ser Leu
Asp Ala Ser --- --- Gly Asp Leu Tyr Thr Thr Ser Ser Gln Leu Thr Leu Pro Ala Thr Gln Cys
Asp Ala Ser --- --- Gly Asp Leu Tyr Thr Thr Ser Ser Gln Leu Thr Leu Pro Ala Thr Gln Cys
Arg Arg Asp --- --- Ser Tyr Tyr Met Thr Ser Ser Gln Leu Ser Thr Pro Leu Gln Gln Trp Arg
Leu Thr Leu --- --- Ser Gly His Tyr Ala Thr Ile Ser Leu Leu Thr Val Ser Gly Ala Trp Ala
Val Leu Arg Gly Gly Lys Tyr Ala Ala Thr Ser Gln Val Leu Leu Pro Ser Lys Asp Val Met Gln
Val Leu Gln Ser --- Ser Gly Leu Tyr Ser Leu Ser Ser Val Val Thr Val Pro Ser Ser Ser Leu

Gly --- Thr Gln Thr Tyr Ile Cys Asn Val Asn His Lys Pro Ser Asn Thr Lys Val Asp Lys Lys
Gly --- Thr Gln Thr Tyr Thr Cys Asn Val Asp His Lys Pro Ser Asn Thr Lys Val Asp Lys Thr
Gly --- Thr Gln Thr Tyr Thr Cys Asn Val Asn His Lys Pro Ser Asn Thr Lys Val Asp Lys Arg
Gly --- Thr Lys Thr Tyr Thr Cys Asn Val Asp His Lys Pro Ser Asn Thr Lys Val Asp Lys Arg
Leu Ala Gly Lys Ser Val Thr Cys His Val Lys His Tyr --- --- --- Thr Asn Pro Ser Gln Asp
Pro Asp Gly Lys Ser Val Thr Cys His Val Lys His Tyr --- --- --- Thr Asn Pro Ser Gln Asp
--- --- Gln Gly Glu Tyr Lys Cys Val Val Gln His Thr Ala Ser Lys Ser Lys Lys Glu Ile Phe
--- --- Lys Gln Met Phe Thr Cys Arg Val Ala His Thr Pro Ser Ser Thr Asp Trp Val Asp Asn
Gly Thr Asp Glu His Val Val Cys Lys Val Gln His Pro --- --- Asn Gly Asn Lys Glu Lys Asn
Gly --- Thr Gln Thr Tyr Thr Cys Asn Val Asp His Lys Pro Ser Asn Thr Lys Val Asp Lys Asp

Val Glu Pro Lys Ser Cys
Val Ala Glu Arg Lys Cys Cys
Val Glu Leu Lys Thr Pro
Val Glu Ser Lys Tyr Gly
Val Thr Val Pro --- Cys
Val Thr Val Pro --- Cys
Arg Trp Pro Glu Ser Pro
Lys Thr Phe Ser Val Cys
Val Pro Leu Pro Val
Val Thr Val Lys Val Cys
```

Fig. 2B

```
Human kappa constant (SEQ ID NO:61):      Arg Thr Val Ala Ala Pro Ser Val Phe Ile Phe Pro
Human lambda constant (SEQ ID NO:62):     Gln Pro Lys Ala Ala Pro Ser Val Thr Leu Phe Pro
Consensus (SEQ ID NO:63):                 Gln Thr Val Ala Ala Pro Ser Val Thr Leu Phe Pro

Pro Ser Asp Glu Gln Leu Lys Ser Gly Thr Ala Ser Val Val Cys Leu Leu Asn Asn Phe Tyr Pro
Pro Ser Ser Glu Glu Leu Gln Ala Asn Lys Ala Thr Leu Val Cys Leu Ile Ser Asp Phe Tyr Pro
Pro Ser Ser Glu Glu Leu Gln Ala Gly Thr Ala Ser Val Val Cys Leu Leu Ser Asp Phe Tyr Pro

Arg Glu Ala Lys Val Gln Trp Lys Val Asp Asn Ala Leu Gln Ser Gly Asn Ser Gln Glu Ser Val
Gly Ala Val Thr Val Ala Trp Lys Ala Asp Ser Ser Pro Val Lys Ala Gly Val Glu Thr Thr Thr
Gly Ala Ala Thr Val Ala Trp Lys Ala Asp Ser Ala Leu Val Ser Gly Gly Val Glu Thr Ser Val

Thr Glu Gln Asp Ser Lys Asp Ser Thr Tyr Ser Leu Ser Ser Thr Leu Thr Leu Ser Lys Ala Asp
Pro Ser Lys Gln Ser Asn Asn Lys --- Tyr Ala Ala Ser Ser Tyr Leu Ser Leu Thr Pro Glu Gln
Thr Ser Gln Asp Ser Asn Asp Ser Thr Tyr Ala Ala Ser Ser Thr Leu Ser Leu Ser Lys Ala Asp

Tyr Glu Lys His Lys Val Tyr Ala Cys Glu Val Thr His Gln Gly Leu Ser Ser Pro Val Thr Lys
Trp Lys Ser His Arg Ser Tyr Ser Cys Gln Val Thr His Glu Gly --- --- Ser Thr Val Glu Lys
Tyr Glu Ser His Lys Val Tyr Ala Cys Glu Val Thr His Glu Gly Leu Ser Ser Thr Val Thr Lys

Ser Phe Asn Arg Gly Glu Cys
Thr Val Ala Pro Thr Glu Cys Ser
Ser Val Ala Arg Gly Glu Cys Ser
```

Fig. 3

DIMERIC FUSION PROTEINS AND MATERIALS AND METHODS FOR PRODUCING THEM

CROSS-REFERENCE TO RELATED APPLICATION

This application claims the benefit of U.S. Provisional Application Ser. No. 60/551,174, filed Mar. 8, 2004, which is herein incorporated by reference.

BACKGROUND OF THE INVENTION

A variety of proteins, including both cell-surface receptors and soluble ligands, require dimerization for proper biological activity. Although dimerization may readily occur in the native biological milieu, it is often problematic for recombinant forms of many proteins, including soluble forms of receptors that are embedded in the cell surface in their native state.

Cell-surface receptors that must dimerize in order to transduce a signal include members of the receptor tyrosine kinase family, the tumor necrosis factor (TNF) receptor family, and the class 1 and class 2 cytokine receptor families. Platelet derived growth factor (PDGF) receptors, for example, dimerize upon ligand binding, resulting in autophosphorylation of tyrosine residues and initiation of intracellular signal transduction. Other examples of receptors that dimerize upon ligand binding include growth hormone receptors, interleukin-2 (IL-2) receptors, IL-3 receptors, IL-5 receptors, IL-6 receptors, granulocyte-macrophage colony stimulating factor (GM-CSF) receptors, oncostatin M (OSM) receptors, leukemia inhibitory factor (LIF) receptors, and ciliary neurotrophic factor (CNTF) receptors. Dimerized receptors include both homodimers and heterodimers. Some receptor polypeptides function as subunits within a plurality of cytokine receptor dimers. See, for example, Cosman, *Cytokine* 5:95-106, 1993.

Naturally occuring soluble forms of many cell-surface receptors are known. These soluble receptors correspond to the ligand-binding domains of their cell-surface counterparts. Soluble cytokine receptors inhibit cytokine responses and act as transport proteins. See, for example, Aggarwal and Puri, "Common and Uncommon Features of Cytokines and Cytokine Receptors: An Overview," in Aggarwal and Puri, eds., *Human Cytokines: Their Role in Disease and Therapy*, Blackwell Science, 1995, 3-24. It has been found that dimerization of soluble receptor polypeptides through the use of fusion proteins may enhance the binding properties of these soluble receptors so that they become therapeutically useful antagonists of their cognate ligands. Typical of such dimeric fusions are immunoglobulin fusions. See, for example, Sledziewski et al., U.S. Pat. Nos. 5,155,027 and 5,567,584; Jacobs et al., U.S. Pat. No. 5,605,690; Wallner et al., U.S. Pat. No. 5,914,111; and Ashkenazi and Chamow, *Curr. Opin. Immunol.* 9:195-200, 1997.

To date, immunoglobulin fusion technology has not provided a commercially viable means to produce heterodimeric proteins. Using currently available technology, co-expression of two different fusion polypeptides in a recombinant cell generally results in a mixture of both homodimers and heterodimers. The costs associated with recovery and purification of heterodimers from the mixture has limited the commercial application of this technology. Thus, there remains a need in the art for an efficient method of producing soluble, dimeric proteins, including soluble receptor dimers and soluble heterodimers.

DESCRIPTION OF THE INVENTION

Within one aspect of the present invention there is provided a first polypeptide fusion consisting of, from amino terminus to carboxyl terminus, P1-L1-D1-$(P2)_n$, wherein P1 is a non-immunoglobulin polypeptide; L1 is a polypeptide linker consisting of from 18 to 32 amino acid residues, wherein x of the residues are cysteine residues and x is an integer from 1 to 8; D1 is a dimerizing domain selected from the group consisting of an immunoglobulin CH1 domain, a T-cell receptor Cα domain, a T-cell receptor Cβ domain, a major histocompatibility complex class I α3 domain, β2-microglobulin, a major histocompatibility complex class II α2 domain, and a major histocompatibility complex class II β2 domain; P2 is a linking polypeptide consisting of from 1 to 29 amino acid residues, wherein at least one of the residues is a cysteine residue; and n is 0 or 1. Within one embodiment, P1 is an extracellular domain of a cell-surface receptor, such as a human receptor. Within another embodiment, P1 is not a member of the immunoglobulin superfamily. Within other embodiments, P1 is selected from the group consisting of IL-17R, IL-20RA, IL-20RB, IL-21R, IL-28RA, IL-31RA, CRF24, and γC. Within a further embodiment, L1 contains exactly two cysteine residues. Within another embodiment, L1 comprises an immunoglobulin hinge or fragment or variant thereof, such as an immunoglobulin hinge variant wherein the cysteine residue corresponding to Eu residue 220 is replaced by serine. Within another embodiment, L1 comprises a human γ1 hinge or fragment or variant thereof. Within an additional embodiment, L1 consists of 18 amino acid residues. Within yet other embodiments, L1 comprises a plurality of glycine residues or L1 comprises a plurality of serine residues. Within related embodiments, L1 comprises $[\text{Gly-Ser-Gly-Ser}]_a$ (SEQ ID NO:2), wherein a is 1 or 2; or $[\text{Gly-Gly-Gly-Ser}]_b$ (SEQ ID NO:3), wherein b is 1 or 2. Within an additional embodiment, L1 comprises a proteolytic cleavage site. Within a further embodiment, D1 is an immunoglobulin CH1 domain, such as a human immunoglobulin CH1 domain. Within yet other embodiments, the immunoglobulin CH1 domain is a γ1 CH1 domain, such as a human γ1 CH1 domain. Within another embodiment, P2 is a portion of an immunoglobulin hinge comprising a cysteine residue. Within a further embodiment, n is 1. Within another embodiment, P2 consists of from 5 to 15 amino acid residues. Within an additional embodiment, P2 contains exactly one cysteine residue.

Within a second aspect of the invention there is provided a second polypeptide fusion consisting of, from amino terminus to carboxyl terminus, P3-L2-D2, wherein P3 is a non-immunoglobulin polypeptide; L2 is a polypeptide linker consisting of from 18 to 32 amino acid residues, wherein y of the residues are cysteine residues and y is an integer from 1 to 8; and D2 is a dimerizing domain selected from the group consisting of an immunoglobulin light chain constant domain, a T-cell receptor Cα domain, a T-cell receptor Cβ domain, a major histocompatibility complex class I α3 domain, β2-microglobulin, a major histocompatibility complex class II α2 domain, and a major histocompatibility complex class II β2 domain. Within one embodiment of the invention, P3 is an extracellular domain of a cell-surface receptor, such as a human receptor. Within another embodiment, P3 is not a member of the immunoglobulin superfamily. Within other embodiments, P3 is selected from the group consisting of IL-17R, IL-20RA, IL-20RB, IL-21R, IL-28RA, IL-31RA, CRF24, and γC. Within further embodiments, L2 contains exactly two cysteine residues, L2 comprises an immunoglobulin hinge or fragment or variant thereof, L2 comprises an immunoglobulin hinge variant wherein the cysteine residue corresponding to Eu residue 220 is replaced by serine, L2 comprises a human γ1 hinge or fragment or variant thereof, or L2 consists of 18 amino acid residues. Within other embodiments, L2 comprises a plurality of glycine residues or L2 comprises a plurality of serine residues. Within related embodiments, L2 comprises [Gly-Ser-Gly-Ser]$_a$ (SEQ ID NO:2), wherein a is 1 or 2; or [Gly-Gly-Gly-Ser]$_b$ (SEQ ID NO:3), wherein b is 1 or 2. Within a further embodiment, L2 comprises a proteolytic cleavage site. Within yet other embodiments, D2 is an immunoglobulin κ light chain constant domain or immunoglobulin λ light chain constant domain.

Within a third aspect of the invention there is provided a polynucleotide encoding the first polypeptide fusion disclosed above. Within one embodiment the polynucleotide is DNA.

Within a fourth aspect of the invention there is provided a polynucleotide encoding the second polypeptide fusion disclosed above. Within one embodiment the polynucleotide is DNA.

Within a fifth aspect of the invention there is provided an expression vector comprising the following operably linked elements: a transcription promoter; a DNA segment encoding the first polypeptide fusion disclosed above; and a transcription terminator.

Within a sixth aspect of the invention there is provided an expression vector comprising the following operably linked elements: a transcription promoter; a DNA segment encoding the second polypeptide fusion disclosed above; and a transcription terminator.

Within a seventh aspect of the invention there is provided a cultured cell into which has been introduced one or both of the expression vectors disclosed above, wherein the cell expresses the DNA segment(s).

Within an eighth aspect of the invention there is provided a dimeric protein consisting of a first polypeptide fusion as disclosed above disulfide bonded to a second polypeptide fusion as disclosed above, wherein each of x and y is an integer from 1 to 8 and x=y. Within one embodiment, P1 and P3 are different. Within another embodiment, n=1. Within a further embodiment, x=2 and y=2. Within other embodiments, one of P1 and P3 is a zcytor7 extracellular domain and the other of P1 and P3 is a DIRS1 extracellular domain; one of P1 and P3 is a zcytor 11 extracellular domain and the other of P1 and P3 is a DIRS1 extracellular domain; one of P1 and P3 is a zalpha 11 extracellular domain and the other of P1 and P3 is an IL-2 receptor γ common extracellular domain; or one P1 and P3 is a PDGF α receptor extracellular domain and the other of P1 and P3 is a PDGF β receptor extracellular domain.

Within a ninth aspect of the invention there is provided a method of making the dimeric protein disclosed above comprising the steps of (a) culturing a cell comprising first and second expression units, wherein the first expression unit comprises a transcription promoter, a first DNA segment encoding the first polypeptide fusion disclosed above, and a transcription terminator; and wherein the second expression unit comprises a transcription promoter, a second DNA segment encoding the second polypeptide fusion disclosed above, and a transcription terminator, whereby the first and second DNA segments are expressed and the encoded polypeptide fusions are produced as a dimeric protein; and (b) recovering the dimeric protein.

Within a tenth aspect of the invention there is provided a homodimeric protein consisting of two second polypeptide fusions as disclosed above, wherein D2 is an immunoglobulin light chain constant domain and wherein said fusions are joined to each other by at least one disulfide bond.

Within an eleventh aspect of the invention there is provided a method of making the homodimeric protein disclosed above comprising the steps of (a) culturing a cell comprising an expression vector comprising the following operably linked elements: a transcription promoter; a DNA segment encoding the second polypeptide fusion disclosed above wherein D2 is an immunoglobulin light chain constant domain; and a transcription terminator, whereby the DNA segment is expressed and the encoded polypeptide fusion is produced as a homodimeric protein; and (b) recovering the homodimeric protein.

These and other aspects of the invention are illustrated by the following detailed description and the attached drawings. Within the drawings:

FIGS. 1A-1B illustrate the amino acid sequence of a portion of a representative human immunoglobulin γ1 heavy chain (SEQ ID NO:1) (based on Ellison et al., *Nucl. Acids Res.* 10:4071, 1982). Amino acid sequence numbers are based on the Eu index (Edelman et al., *Proc. Natl. Acad. Sci. USA* 63:78-85, 1969; Kabat et al., *Sequences of Proteins of Immunological Interest*, US Department of Health and Human Services, NIH, Bethesda, Md., 1991). The Cys residues normally involved in disulfide bonding to the light chain constant region (LC) and heavy chain constant region (HC) are indicated. Boundaries of the $C_H1$, hinge, $C_H2$, and $C_H3$ domains are shown.

FIGS. 2A-2B show an alignment of representative human CH1 domain sequences and a consensus sequence derived from the alignment. Sequence gaps are indicated by " - - - ".

FIG. 3 shows an alignment of representative human light chain constant domain sequences and a consensus sequence derived from the alignment. Sequence gaps are indicated by " - - - ".

All references cited herein are incorporated by reference in their entirety.

As used herein, the phrase "a cultured cell into which has been introduced an expression vector" includes cells that have been physically manipulated to contain the vector, as well as progeny of the manipulated cells when the progeny also contain the vector.

The terms "amino-terminal" (or "N-terminal") and "carboxyl-terminal" (or "C-terminal") are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "corresponding to", when applied to positions of amino acid residues in sequences, means corresponding positions in a plurality of sequences when the sequences are optimally aligned.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

An "immunoglobulin" is a serum protein which functions as an antibody in a vertebrate organism. Five classes of "immunoglobulin," or antibody, protein (IgG, IgA, IgM, IgD, and IgE) have been identified in higher vertebrates. IgG comprises the major class; it normally exists as the second most abundant protein found in plasma. In humans, IgG consists of four subclasses, designated IgG1, IgG2, IgG3, and IgG4. The heavy chain constant regions of the IgG class are identified with the Greek symbol γ. For example, immunoglobulins of the IgG1 subclass contain a γ1 heavy chain constant region. Each immunoglobulin heavy chain possesses a constant region that consists of constant region protein domains ($C_H1$, hinge, $C_H2$, and $C_H3$) that are essentially invariant for a given subclass in a species. DNA sequences encoding human and non-human immunoglobulin chains are known in the art. See, for example, Ellison et al., *DNA* 1:11-18, 1981; Ellison et al., *Nucleic Acids Res.* 10:4071-4079, 1982; Kenten et al., *Proc. Natl. Acad. Sci. USA* 79:6661-6665, 1982; Seno et al., *Nuc. Acids Res.* 11:719-726, 1983; Riechmann et al., *Nature* 332:323-327, 1988; Amster et al., *Nuc. Acids Res.* 8:2055-2065, 1980; Rusconi and Kohler, *Nature* 314:330-334, 1985; Boss et al., *Nuc. Acids Res.* 12:3791-3806, 1984; Bothwell et al., *Nature* 298:380-382, 1982; van der Loo et al., *Immunogenetics* 42:333-341, 1995; Karlin et al., *J. Mol. Evol.* 22:195-208, 1985; Kindsvogel et al., *DNA* 1:335-343, 1982; Breiner et al., *Gene* 18:165-174, 1982; Kondo et al., *Eur. J. Immunol.* 23:245-249, 1993; and GenBank Accession No. J00228. For a review of immunoglobulin structure and function see Putnam, *The Plasma Proteins*, Vol V, Academic Press, Inc., 49-140, 1987; and Padlan, *Mol. Immunol.* 31:169-217, 1994.

The term "immunoglobulin CH1 domain" denotes a wild-type immunoglobulin heavy chain CH1 constant domain or a variant thereof, wherein the variant folds into the higher order structure characteristic of native immunoglobulin heavy chain constant domains (two twisted β sheets stabilized by a single disulfide bond; see, for example, Amzel and Poljak, *Annu. Rev. Immunol.* 48:961-997, 1979) and is capable of dimerizing with an immunoglobulin light chain constant domain. A representative wild-type human γ1 heavy chain is shown in FIGS. 1A-1B (SEQ ID NO:1). The CH1 domain extends from Eu residue 118 to Eu residue 215 (residues 1 to 98 of SEQ ID NO:1) according to the domain boundaries disclosed by Edelman et al., *Proc. Natl. Acad. Sci. USA* 63:78-85, 1969. Those skilled in the art will recognize that domain boundaries are approximate and may vary by ±5 residues depending upon the criteria used to identify them. Immunoglobulin CH1 domains include, for example, the CH1 domains of human gamma1 (SEQ ID NO:48), gamma2 (SEQ ID NO:49), gamma3 (SEQ ID NO:50), gamma4 (SEQ ID NO:51), alpha1 (SEQ ID NO:52), alpha2 (SEQ ID NO:53), delta (SEQ ID NO:54), epsilon (SEQ ID NO:55), and mu (SEQ ID NO:56) immunoglobulin chains, as well as a consensus human CH1 domain (SEQ ID NO:57) based on an alignment of the wild-type human CH1 domains as shown in SEQ ID NOS: 48-56 (FIGS. 2A-2B). SEQ ID NOS:48-57 are extended at their carboxyl termini relative the the CH1 domain as shown in FIG. 1. Variants of native Ig heavy chain constant domains include, without limitation, those disclosed by Lesk and Chothia, *Nature* 335:188-190, 1988 and Carter et al., U.S. Pat. No. 5,807,706. Variants of native Ig CH1 domains will exhibit a pair-wise level of sequence identity to wild-type CH1 domains at least as great as the minimum pair-wise identity exhibited in the alignment shown in FIGS. 2A-2B. Representative mouse epsilon, gamma2a, and gamma3 CH1 domain sequences are shown in SEQ ID NOS:58, 59, and 60, respectively.

An "immunoglobulin hinge" is that portion of an immunglobulin heavy chain connecting the variable and CH1 domains. Within SEQ ID NO:1, the hinge is approximately residues 99 to 113 (Eu residues 216-230 as shown in FIG. 1A).

The term "immunoglobulin light chain κ or λ constant region" denotes a native immunoglobulin light chain constant domain of the κ (e.g., SEQ ID NO:61) or λ (e.g., SEQ ID NO:62) isotype, or a variant thereof, wherein the variant folds into the higher order structure characteristic of native immunoglobulin light chains constant domains and is capable of dimerizing with an immunoglobulin CH1 domain. Variants include a consensus light chain constant region as shown in SEQ ID NO:63, as well as other variants that exhibit a pair-wise level of sequence identity to wild-type light chain constant domains at least as great as the minimum pair-wise identity exhibited in the alignment shown in FIG. 3.

The "immunoglobulin superfamily" is a functionally diverse family of proteins having structural similarities to immunoglobulins. These proteins have structural features, including disulfide bonds, characteristic of immunoglobulin constant and/or variable region domains. Many members of the immunoglobulin superfamily are cell-surface proteins that perform a recognition role.

"Non-covalent associations" between polypeptides or proteins include hydrogen bonding, steric interactions, hydrophobic interactions, and ionic interactions.

A "non-immunoglobulin polypeptide" is a polypeptide that is not an immunoglobulin or fragment of an immunoglobulin. However, the term "non-immunoglobulin polypeptide" does not exclude polypeptides that are members (or fragments of members) of the immunoglobulin superfamily or that contain immunoglobulin-like domains, so long as they are not themselves immunoglobulins. Non-immunoglobulin polypeptides that are members of the immunoglobulin superfamily include, without limitation, PDGF alpha receptor, PDGF beta receptor, CTLA4, CSF-1 receptor, stem cell factor receptor, and the like.

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator. When referring to polypeptides, "operably linked" includes both covalently (e.g., by disulfide bonding) and non-covalently (e.g., by hydrogen bonding, hydrophobic interactions, or salt-bridge interactions) linked sequences, wherein the desired function(s) of the sequences are retained.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

A "segment" is a portion of a larger molecule (e.g., polynucleotide or polypeptide) having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The present invention provides dimeric fusion proteins, including homodimers and heterodimers. Within certain embodiments of the invention the dimers are heterodimers consisting of first and second polypeptide fusions. The first polypeptide fusion comprises a first dimerizing domain and the second polypeptide fusion comprises a second dimerizing domain. When the first and second fusions are co-expressed in a recombinant host cell, the first and second dimerizing domains associate with each other to form a heterodimer. The dimer is stabilized by the formation of one or more interchain disulfide bonds. The invention is particularly useful for the production of heterodimeric binding partner pairs, including soluble forms of heterodimeric receptors. However, as shown in Example 6, a second polypeptide fusion of the invention comprising an immunoglobulin light chain constant domain as the dimerizing domain forms a disulfide-bonded homodimer when expressed in the absence of the first polypeptide fusion.

The first polypeptide fusion consists of, from amino terminus to carboxyl terminus: a first non-immunoglobulin polypeptide; a polypeptide linker consisting of from 18 to 32 amino acid residues, wherein from 1 to 8 of the residues are cysteine residues; a first dimerizing domain; and, optionally, a linking polypeptide of from 1 to 29 amino acid residues including at least one cysteine residue. Within certain embodiments of the invention, the first dimerizing domain is an immunoglobulin CH1 domain.

The second polypeptide fusion consists of, from amino terminus to carboxyl terminus: a second non-immunoglobulin polypeptide; a polypeptide linker consisting of from 18 to 32 amino acid residues, wherein from 1 to 8 of said residues are cysteine residues; and a second dimerizing domain. Within certain embodiments of the invention the second dimerizing domain is an immunoglobulin light chain constant domain selected from the group consisting of Cκ and Cλ.

Within certain embodiments of the invention, the first and second non-immunoglobulin polypeptides have functions that are to be combined in a single molecule. Such functions can be disparate or complementary. "Disparate functions" is used herein to indicate distinct biological functions or properties that reside in individual polypeptides that do not naturally function in concert. Examples of polypeptides having disparate functions include targeting proteins that bind to cell-surface structures, cytotoxins, growth factors, enzymes, hormones, and cytokines. Thus, proteins of the present invention can combine, for example, a targeting protein and a cytotoxin so that the cytotoxin can be delivered to a particular cell or set of cells. "Complementary functions" is used herein to indicate that the first and second polypeptides function together in the natural milieu in a coordinated manner, and includes functional combinations that, in their natural occurance, result from covalent interactions or non-covalent interactions between the first and second polypeptides, or from spatial effects involving additional molecules. Typical of such complementary functions are the dimerization or other multimerization of cell-surface receptors and their ligands. As discussed above, receptors can exist in the cell membrane as pre-formed dimers or may form non-covalent dimers upon ligand binding. Higher order clustering of receptors has also been reported (e.g., Schwartz et al., *Nature Immunol.* 3:427-434, 2002).

Within certain embodiments of the invention the first and second non-immunoglobulin polypeptides are first and second binding partner polypeptides that functionally interact with each other to non-covalently associate with one or more additional polypeptides or proteins to perform a biological function. In general, the biological function is at least in part dependent, qualitatively or quantitatively, upon the association between the associated binding partner polypeptides and the additional polypeptide(s) or protein(s). Ligand-receptor binding is representative of such associations. Many ligands and receptors are multimeric. Cell-surface receptors may dimerize upon binding to dimeric ligands (e.g., PDGF receptors), receptors may exist as preformed dimers (e.g., insulin receptor), or ligand binding may result in the formation of higher order arrays of pre-existing dimeric receptors (e.g., CTLA-4). Receptor monomers may associate covalently or non-covalently. If the first and second binding partner polypeptides are soluble receptor polypeptides, their binding of ligand may be enhanced by their association (dimerization). If the first and second binding partner polypeptides are soluble ligands, dimerization may be required for binding to and/or activating cell surface receptors. Examples of binding partner polypeptides that can be used within the present invention include, without limitation, PDGF A, PDGF B, PDGF C, PDGF D, IL-12 p35 subunit, IL-12 p40 subunit, IL-23 p19 subunit, IL-27 p28 subunit, EBI3, zlut1 (GPHB5) (US Patent Application Publication No. 20020160953A), zsig51 (GPHA2) (U.S. Pat. No. 6,573,363), PDGF receptor α (PDGF-Rα), PDGF-Rβ, zalpha11 (IL-21R) (US Patent Application Publication No. 20030148447A), zcytor7 (IL-20RA) (U.S. Pat. No. 5,945,511), DIRS1 (IL-20RB) (WIPO Publication No. WO 99/27103), zcytor11 (IL-22RA1) (U.S. Pat. No. 5,965,704), zcytor17 (IL-31RA) (US Patent Application Publication No. 20030096339A), zcytor19 (IL-28RA) (US Patent Application Publication No. 20030027253A), CRF2-4 (IL10-Rβ), TACI (U.S. Pat. No. 5,969,102), BCMA, BAFF receptor, TNF receptors, growth hormone receptor, KH97 (human common beta subunit), gp130, LIF receptor (LIF-Rβ), oncostatin M receptor (OSM-Rβ) IL-2Rβ, IL-2 receptor γ common subunit (γC), IL-3Rα, IL-3Rβ, IL-4Rα, IL-6Rα, IL-11Rα, IL-12Rβ1, IL-12Rβ2, IL-13Rα1, IL13-Rα2, IL-17R, IL-23R, OPG, Fas, WSX-1 (TCCR) (U.S. Pat. No. 5,792,850), CNTF-Rα, and GM-CSF-Rα.

Exemplary combinations of first and second non-immunoglobulin polypeptides are shown in Table 1.

TABLE 1

| First non-Ig polypeptide | Second non-Ig polypeptide |
|---|---|
| PDGF A | PDGF B |
| IL-12 p35 | IL-12 p40 |
| IL-12 p35 | EBI3 |
| IL-12 p40 | IL-12 p40 |
| IL-27 p28 | EBI3 |
| IL-12 p40 | IL-23 p19 |
| GPHB5 | GPHA2 |
| EBI3 | EBI3 |
| PDGF A | PDGF A |
| PDGF B | PDGF B |
| PDGF C | PDGF C |
| PDGF D | PDGF D |
| PDGF-Rα | PDGF-Rβ |
| zcytor7 | DIRS1 |
| zcytor11 | DIRS1 |
| zcytor17 | OSM-Rβ |
| zcytor19 | CRF2-4 |
| WSX1 | gp130 |
| IL-4Rα | γC |
| IL-23R | IL-12Rβ1 |
| IL-4Rα | IL-13Rα1 |
| IL-3Rβ | IL-5Rα |
| IL-3Rβ | GM-CSF-Rα |
| IL-3Rβ | IL-3Rα |
| IL-12Rβ1 | IL-12Rβ2 |
| IL-21R | γC |
| IL-6Rα | gp130 |
| OSM-Rβ | gp130 |
| LIF-Rβ | gp130 |
| CNTFR | gp130 |
| PDGF B | PDGF A |
| IL-12 p40 | IL-12 p35 |
| EBI3 | IL-12 p35 |
| IL-23 p19 | IL-12 p40 |
| EBI3 | IL-27 p28 |
| GPHA2 | GPHB5 |
| PDGF-Rβ | PDGF-Rα |
| DIRS1 | zcytor7 |
| DIRS1 | zcytor11 |
| OSM-Rβ | zcytor17 |
| CRF2-4 | zcytor19 |
| gp130 | WSX1 |
| γC | IL-4Rα |
| IL-12Rβ1 | IL-23R |
| IL-13Rα1 | IL-4Rα |
| IL-5Rα | IL-3Rβ |
| GM-CSF-Rα | IL-3Rβ |
| IL-3Rα | IL-3Rβ |
| IL-12Rβ2 | IL-12Rβ1 |
| γC | IL-21R |
| Gp130 | IL-6Rα |
| Gp130 | OSM-Rβ |
| Gp130 | LIF-Rβ |
| Gp130 | CNTFR |

The polypeptide linker consists of from 18 to 32 amino acid residues, wherein from 1 to 8 of said residues are cysteine residues. Within a preferred embodiment of the invention, each linker contains exactly two cysteine residues. Within another embodiment, the linker is 18 amino acid residues in length. The linker is designed to provide sufficient space and flexibility between the dimerizing domain and the non-immunoglobulin polypeptide within each of the first and second polypeptide fusions to allow the first and second non-immunoglobulin polypeptides to perform their intended functions within the dimeric protein. Those skilled in the art will recognize that the precise spacing, and hence the precise length of each polypeptide linker, will depend upon the choice of each of the first and second non-immunoglobulin polypeptides and its function. For example, binding partner polypeptides will generally associate in a dimeric structure, while polypeptides having disparate functions may exist in spaced relationship to each other. In any event, the linker length and composition are selected to provide the desired spacing and degree of flexibility, while also providing for one or more interchain disulfide bonds to stabilize the desired conformation.

Required linker lengths can be determined through molecular modeling of the first and second non-immunoglobulin polypeptides, such as by analysis of crystal structure data for native dimers. Such methods can also be used to determine the distance between the termini of the immunoglobulin domain components of the fusion protein. One skilled in the art can then calculate the required minimum linker length based on these determinations. In general, a maximum length of approximately 3 Å per amino acid residue is used as a basis for predicting linker length. To ensure sufficient length and flexibility in the linker it is often desirable to exceed the predicted minimum required length. Calculation of the effective length of a polypeptide in solution is routine in the art. See, for example, Creighton, *Proteins: Structures and Molecular Properties,* $2^{nd}$ edition, W. H. Freeman and Company, 1993, Chapter 5.

Within certain embodiments of the invention the polypeptide linker comprises an immunoglobulin hinge or a fragment or variant of an immunoglobulin hinge region. Within one embodiment of the invention the N-terminal most cysteine residue (Eu residue 220; residue 103 of SEQ ID NO:1), which in an assembled antibody forms a disulfide bond with an immunoglobulin light chain, is omitted from the hinge, either by replacement with another amino acid residue (e.g., Ser) or by deletion or truncation. Other changes in the hinge sequence can also be made. For example the Lys residue (Eu 218; residue 101 of SEQ ID NO:1) can be changed to Arg. The polypeptide linker can thus comprise an immunoglobulin hinge region that contains two cysteine residues that form disulfide bonds with the polypeptide linker on the other chain. An immunoglobulin hinge region can be obtained from any immunoglobulin heavy chain. Gamma (IgG) hinge regions, such as the γ1 hinge, have been well characterized and are conveniently used within the present invention. Those skilled in the art will recognize that different hinge polypeptides will provide different angles within the dimeric proteins, thus specific hinge polypeptides may be selected to optimize the overall structure of the molecule. Molecular modeling techniques, as disclosed above, can be used to select the optimal hinge to be used with any pair of non-immunoglobulin polypeptides.

Non-hinge residues within the linker polypeptide are selected to provide an overall hydrophilic character and to be non-immunogenic and flexible. As used herein, a "flexible" linker is one that lacks a substantially stable higher-order conformation in solution, although regions of local stability are permissible. In general, small, polar, and hydrophilic residues are preferred, and bulky and hydrophobic residues are undesirable. Areas of local charge are to be avoided; if the linker polypeptide includes charged residues, they will ordinarily be positioned so as to provide a net neutral charge within a small region of the polypeptide. It is therefore preferred to place a charged residue adjacent to a residue of opposite charge. In general, preferred residues for inclusion within the linker polypeptide include Gly, Ser, Ala, Thr, Asn, and Gln; more preferred residues include Gly, Ser, Ala, and Thr; and the most preferred residues are Gly and Ser. In general, Phe, Tyr, Trp, Pro, Leu, Ile, Lys, and Arg residues will be avoided (unless present within an immunoglobulin hinge region of the linker), Pro residues due to their hydrophobicity and lack of flexibility, and Lys and Arg residues due to potential immunogenicity. However, these less desirable residues may be included to provide a specific proteolytic cleavage site as disclosed below. Cys residues will be included, as disclosed above, so as to provide for disulfide bonding. Exemplary linkers are those comprising the structure $[\text{Gly-Ser-Gly-Ser}]_a$ (SEQ ID NO:2), wherein a is 1 or 2, and $[\text{Gly-Gly-Gly-Ser}]_b$ (SEQ ID NO:3), wherein b is 1 or 2. The sequence of the linker will also be designed to avoid unwanted proteolysis. However, within certain embodiments of the invention, the linker polypeptide comprises a proteolytic cleavage site to facilitate separation of the dimerizing domains from the remainder of the molecule, leaving intact the disulfide bond(s) joining the first and second non-immunoglobulin polypeptides through their respective linker polypeptides. Exemplary proteolytic cleavage sites include sequences cleaved by plasmin, thrombin, factor Xa, enterokinase, furin, rhinovirus 3C protease, renin, collagenase, and caspase-3. The use of these and other proteases to cleave fusion proteins is known in the art. See, for example, Rubinstein et al., WO 00/61768; van de Ven et al., U.S. Pat. No. 5,935,815; Sgarlato, U.S. Pat. No. 5,935,824; and Fischer et al., U.S. Pat. No. 6,010,844. Thrombin cleaves after the dipeptide sequence Pro-Arg. Enterokinase cleaves after the pentapeptide sequence Asp-Asp-Asp-Asp-Lys (SEQ ID NO:4). Factor Xa cleaves after the sequence Ile-Glu-Gly-Arg (SEQ ID NO:5). Plasmin cleaves after the sequence Arg-Pro. The human rhinovirus 3C protease cleaves Gln-Gly peptide bonds, such as in the sequence Leu-Glu-Val-Leu-Phe-Gln-Gly-Pro (SEQ ID NO:6). Furin cleaves after Arg-Xaa-Lys/Arg-Arg (SEQ ID NO:7). Renin cleaves between adjacent leucine residues in the sequence Pro-Phe-His-Leu-Leu-Val-Tyr (SEQ ID NO:8). Collagenase cleaves within the sequence Pro-Xaa-Gly-Pro-Xaa (SEQ ID NO:9). Caspase-3 cleaves after the sequence Asp-Glu-Val-Asp (SEQ ID NO:10). Those skilled in the art will recognize that these proteolytic enzymes may also cleave at related sequences.

The first dimerizing domain is an immunoglobulin constant domain-like segment of an immunoglobulin or immunoglobulin superfamily member that is capable of dimerizing with a second dimerizing domain as disclosed below. First dimerizing domains within the present invention include immunoglobulin CH1 domains, T-cell receptor Cα and Cβ domains, major histocompatibility complex (MHC) class I α3 domains, β2-microglobulin, and MHC class II $\alpha_2$ and $\beta_2$ chains. These molecules are known in the art. See, for example, Orr et al., *Biochemistry* 18:5711-5720, 1979; Orr et al., *Nature* 282:266-270, 1979; Kaufman et al., *Cell* 36:1-13, 1984; Kronenberg et al., *Ann. Rev. Immunol.* 4:529-591, 1986; Lew et al., *Immunology* 57:3-18, 1986; Williams and Barclay, *Ann. Rev. Immunol.* 6:381405, 1988; and Suggs et al., *Proc. Natl. Acad. Sci. USA* 78:6613-6617, 1981.

The immunoglobulin CH1 domain is capable of non-covalently pairing with an immunoglobulin light chain κ or λ constant region. As disclosed above, the CH1 domain can be a CH1 domain from the γ, α, μ, ε, or δ classes of immunoglobulins, or a variant of a wild-type domain. Within the γ class, a CH1 domain from any of the γ1, γ2, γ3, or γ4 subclasses can be used. Within one embodiment, a γ1 CH1 domain is used. Both human and non-human sequences can be used. As disclosed in more detail below, Eu residue 150 (Phe) in a γ1 CH1 domain (residue 33 of SEQ ID NO:1) can be replaced with an Arg residue.

Other dimerizing domains can also be used within the invention. T-cell receptor (TCR) C1 domains of α and β receptors (Cα and Cβ domains) are capable of non-covalently pairing with each other. MHC class I α3 domains non-covalently bind to β2-microglobulin. MHC class II $\alpha_2$ and $\beta_2$ domains non-covalently bind to each other.

The optional linking polypeptide is a polypeptide consisting of from 1 to 29 amino acid residues wherein at least one of said residues is a cysteine residue. Within one embodiment of the invention, the linking polypeptide is nine residues in length. Within other embodiments the linking polypeptide contains not more than 12 cysteine residues, not more than 2 cysteine residues, or exactly one cysteine residue. Within other embodiments, the linking polypeptide is a portion of an immunoglobulin hinge region comprising the cysteine residue that forms a disulfide bond with an immunoglobulin light chain (Eu residue 220).

The second dimerizing domain is an immunoglobulin constant domain-like segment of an immunoglobulin or immunoglobulin superfamily member that is capable of dimerizing with the first dimerizing domain. Second dimerizing domains within the present invention include immunoglobulin light chain constant domains, T-cell receptor Cα and Cβ domains, major histocompatibility complex (MHC) class I $\alpha_3$ domains, β2-microglobulin, and MHC class II $\alpha_2$ and $\beta_2$ domains. As disclosed above, Ig CH1 domains dimerize with Ig light chain constant domains, T-cell receptor Cα and Cβ domains are capable of non-covalently pairing with each other, MHC class I $\alpha_3$ domains non-covalently bind to β2-microglobulin, and MHC class II $\alpha_2$ and $\beta_2$ domains non-covalently bind to each other. Thus, first and second dimerizing domains are selected as shown in the following Table 2.

TABLE 2

| First Dimerizing Domain | Second Dimerizing Domain |
|---|---|
| Ig CH1 | Ig light chain constant |
| TCR Cα | TCR Cβ |
| TCR Cβ | TCR Cα |
| MHC class I $\alpha_3$ | β2-microglobulin |
| β2-microglobulin | MHC class I $\alpha_3$ |
| MHC class II $\alpha_2$ | MHC class II $\beta_2$ |
| MHC class II $\beta_2$ | MHC class II $\alpha_2$ |

When an immunoglobulin light chain constant domain is the second dimerizing domain, it is preferred to include within the domain the C-terminal cysteine residue (Eu residue 214; Edelman et al., ibid.) (residue 107 of SEQ ID NO:61 or residue 104 of SEQ ID NO:62). Inclusion of this cysteine residue permits stabilization of the dimer structure by disulfide bonding to a cysteine residue within the optional linking polypeptide within the first polypeptide fusion.

Non-immunoglobulin polypeptides, hinge regions, and first and second dimerizing domains used within the present invention can be obtained from a variety of species. If the dimeric protein is to be used therapeutically in humans, it is preferred that human polypeptide sequences be employed. However, non-human sequences can be used, as can variant sequences. For other uses, including in vitro diagnostic uses and veterinary uses, polypeptide sequences from humans or non-human animals can be employed, although sequences from the same species as the patient may be preferred for in vivo veterinary use or for in vitro uses where species specificity of intermolecular reactions is present. Thus, polypeptides for use within the present invention can be, without limitation, human, non-human primate, rodent, canine, feline, equine, bovine, ovine, porcine, lagomorph, and avian polypeptides, as well as variants thereof.

The present invention also provides polynucleotide molecules, including DNA and RNA molecules, that encode the first and second fusion polypeptides disclosed above. The polynucleotides of the present invention include both single-stranded and double-stranded molecules. DNA sequences encoding immunoglobulins and non-immunoglobulin polypeptides, including receptor polypeptides and other binding partner polypeptides, are known in the art. Additional DNA sequences encoding immunoglobulins and non-immunoglobulin polypeptides can be readily generated by those of ordinary skill in the art based on the genetic code. Counterpart RNA sequences can be generated by substitution of U for T. Those skilled in the art will readily recognize that, in view of the degeneracy of the genetic code, considerable sequence variation is possible among polynucleotide molecules encoding a given polypeptide.

Methods for preparing DNA and RNA are well known in the art. Complementary DNA (cDNA) clones are prepared from RNA that is isolated from a tissue or cell that produces large amounts of RNA encoding a polypeptide of interest. Total RNA can be prepared using guanidine HCl extraction followed by isolation by centrifugation in a CsCl gradient (Chirgwin et al., *Biochemistry* 18:52-94, 1979). Poly $(A)^+$ RNA is prepared from total RNA using the method of Aviv and Leder (*Proc. Natl. Acad. Sci. USA* 69:1408-1412, 1972). Complementary DNA is prepared from poly$(A)^+$ RNA using known methods. In the alternative, genomic DNA can be isolated. For some applications (e.g., expression in transgenic animals) it may be advantageous to use a genomic clone, or to modify a cDNA clone to include at least one genomic intron. Methods for identifying and isolating cDNA and genomic clones are well known and within the level of ordinary skill in the art, and include the use of the sequences disclosed herein, or parts thereof, for probing or priming a library. Polynucleotides encoding polypeptides of interest are identified and isolated by, for example, hybridization or polymerase chain reaction ("PCR", Mullis, U.S. Pat. No. 4,683,202). Expression libraries can be probed with antibodies to the polypeptide of interest, receptor fragments, or other specific binding partners.

The polynucleotides of the present invention can also be prepared by automated synthesis. The production of short, double-stranded segments (60 to 80 bp) is technically straightforward and can be accomplished by synthesizing the complementary strands and then annealing them. Longer segments (typically >300 bp) are assembled in modular form from single-stranded fragments that are from 20 to 100 nucleotides in length. Automated synthesis of polynucleotides is within the level of ordinary skill in the art, and suitable equipment and reagents are available from commercial suppliers. See, in general, Glick and Pasternak, *Molecular Biotechnology, Principles & Applications of Recombinant DNA*, ASM Press, Washington, D.C., 1994; Itakura et al., *Ann. Rev. Biochem.* 53: 323-356, 1984; and Climie et al., *Proc. Natl. Acad. Sci. USA* 87:633-637, 1990.

The polypeptide fusions of the present invention can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook et al., *Molecular Cloning: A Laboratory Manual,* 2nd ed., Cold Spring Harbor Laboratory Press, Cold Spring Harbor, N.Y., 1989, and Ausubel et al., eds., *Current Protocols in Molecular Biology*, Green and Wiley and Sons, NY, 1993.

In general, a DNA sequence encoding a polypeptide fusion is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a polypeptide fusion into the secretory pathway of a host cell, a secretory signal sequence is provided in the expression vector. The secretory signal sequence may be that of the native non-immunoglobulin polypeptide, or may be derived from another secreted protein (e.g., t-PA; see, U.S. Pat. No. 5,641,655) or synthesized de novo. An engineered cleavage site may be included at the junction between the secretory peptide and the remainder of the polypeptide fusion to optimize proteolytic processing in the host cell. The secretory signal sequence is operably linked to the DNA sequence encoding the polypeptide fusion, i.e., the two sequences are joined in the correct reading frame and positioned to direct the newly synthesized polypeptide fusion into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Expression of polypeptide fusions via a host cell secretory pathway is expected to result in the production of dimeric proteins. Dimers may also be assembled in vitro upon incubation of component polypeptides under suitable conditions. In general, in vitro assembly will include incubating the protein mixture under denaturing and reducing conditions followed by refolding and reoxidation of the polypeptides to form dimers. Recovery and assembly of proteins expressed in bacterial cells is disclosed below.

Cultured mammalian cells are suitable hosts for use within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S.

Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g. CHO-K1, ATCC No. CCL 61; CHO-DG44, Urlaub et al., *Proc. Natl. Acad. Sci. USA* 77:4216-4220, 1980) cell lines. Additional suitable cell lines are known in the art and available from public depositories such as the American Type Culture Collection, Manassas, Va. Strong transcription promoters can be used, such as promoters from SV40, cytomegalovirus, or myeloproliferative sarcoma virus. See, e.g., U.S. Pat. No. 4,956,288 and U.S. Patent Application Publication No. 20030103986. Other suitable promoters include those from metallothionein genes (U.S. Pat. Nos. 4,579,821 and 4,601,978) and the adenovirus major late promoter. Expression vectors for use in mammalian cells include pZP-1, pZP-9, and pZMP21, which have been deposited with the American Type Culture Collection, 10801 University Blvd., Manassas, Va. USA under accession numbers 98669, 98668, and PTA-5266, respectively, and derivatives of these vectors.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." An exemplary selectable marker is a gene encoding resistance to the antibiotic neomycin. Selection is carried out in the presence of a neomycin-type drug, such as G418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g. hygromycin resistance, multi-drug resistance, puromycin acetyltransferase) can also be used. Cell-surface markers and other phenotypic selection markers can be used to facilitate identification of transfected cells (e.g., by fluorescence-activated cell sorting), and include, for example, CD8, CD4, nerve growth factor receptor, green fluorescent protein, and the like.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci. (Bangalore)* 11:47-58, 1987. Transformation of insect cells and production of foreign polypeptides therein is disclosed by Guarino et al., U.S. Pat. No. 5,162,222 and WIPO publication WO 94/06463.

Insect cells can be infected with recombinant baculovirus, commonly derived from *Autographa californica* nuclear polyhedrosis virus (AcNPV). See, King and Possee, *The Baculovirus Expression System: A Laboratory Guide*, Chapman & Hall, London; O'Reilly et al., *Baculovirus Expression Vectors: A Laboratory Manual*, Oxford University Press., New York, 1994; and Richardson, Ed., *Baculovirus Expression Protocols. Methods in Molecular Biology*, Humana Press, Totowa, N.J., 1995. Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, Md.). The transfer vector (e.g., PFASTBAC1; Life Technologies) contains a Tn7 transposon to move the DNA encoding the protein of interest into a baculovirus genome maintained in *E. coli* as a large plasmid called a "bacmid." See, Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. Using techniques known in the art, a transfer vector encoding a polypeptide fusion is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the polypeptide fusion is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, Calif.). See, in general, Glick and Pasternak, ibid. See also, U.S. Pat. No. 5,300,435. Serum-free media are used to grow and maintain the cells. Suitable media formulations are known in the art and can be obtained from commercial suppliers. The cells are grown up from an inoculation density of approximately $2\text{-}5\times10^5$ cells to a density of $1\text{-}2\times10^6$ cells, at which time a recombinant viral stock is added at a multiplicity of infection (MOI) of 0.1 to 10, more typically near 3. Procedures used are generally described in available laboratory manuals (e.g., King and Possee, ibid.; O'Reilly et al., ibid.; Richardson, ibid.).

Fungal cells, including yeast cells, can also be used within the present invention. Yeast species of particular interest in this regard include *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii*, and *Candida maltosa* are known in the art. See, for example, Gleeson et al., *J. Gen. Microbiol.* 132:3459-3465, 1986; Cregg, U.S. Pat. No. 4,882,279; and Raymond et al., *Yeast* 14:11-23, 1998. *Aspergillus* cells may be utilized according to the methods of McKnight et al., U.S. Pat. No. 4,935,349. Methods for transforming *Acremonium chrysogenum* are disclosed by Sumino et al., U.S. Pat. No.

5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a polypeptide fusion in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine HCl or urea. The denatured polypeptide can then be refolded and dimerized by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted polypeptides can be recovered from the periplasmic space in a soluble and functional form by disrupting the cells (by, for example, sonication or osmotic shock) and recovering the protein, thereby obviating the need for denaturation and refolding. See, for example, Lu et al., *J. Immunol. Meth.* 267:213-226, 2002.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

When the linker polypeptide segment comprises a proteolytic cleavage site, the fusion proteins of the present invention can be cleaved within the host cell to remove the dimerizing domain if the host cell produces a protease that cleaves at the cleavage site. If the host cell does not naturally produce the protease, it can be transfected to co-express the protease and the fusion protein. See, for example, U.S. Pat. Nos. 5,648,254 and 5,935,815.

Proteins of the present invention that contain a cleavage site in the linker polypeptide can also be cleaved in vitro according to conventional methods. The use of proteases for processing recombinant proteins is routine in the art and includes the use of immobilized proteases. See, for example, U.S. Pat. No. 6,010,844. Specific reaction conditions are based on the protease to be used and will be adjusted to minimize unwanted proteolysis with the first polypeptide segment. In general, such parameters as reaction time and ratio of protease to substrate will be adjusted to obtain the desired result.

Proteins of the present invention are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising an immunoglobulin heavy chain polypeptide can be purified by affinity chromatography on immobilized protein A. Additional purification steps, such as gel filtration, can be used to obtain the desired level of purity or to provide for desalting, buffer exchange, and the like.

The proteins of the present invention can be used for diagnosis, therapy, or research to provide one or more activities associated with the first and second non-immunoglobulin polypeptides. Such activities include, without limitation, receptor binding, receptor activation, and ligand binding. Those skilled in the art will readily envision a range of uses for the proteins. Therapeutic uses include, for example, use as cytokine antagonists, such as for the treatment of cancers or immunological disorders, and as growth factor agonists, such as to promote tissue growth or healing or to promote development of vasculature or other tissue. Diagnostic uses include, for example, use as targeting agents for radioisotopes or other labels, for detecting the presence of molecules on cell surfaces or in biological fluids or extracts, or as controls in in vitro assays. Within research the proteins of the present invention can be used, for example, for labeling cells, assaying for the presence of cell-surface receptors or soluble molecules, and to study the biology of non-immunoglobulin polypeptides or their binding partners.

For pharmaceutical use, the proteins of the present invention are formulated for local or systemic (particularly intravenous or subcutaneous) delivery according to conventional methods. In general, pharmaceutical formulations will include a protein of the present invention in combination with a pharmaceutically acceptable delivery vehicle. Delivery vehicles can be aqueous, lipidic, semi-solid or solid as appropriate to the condition to be treated and mode of delivery. Pharmaceutically acceptable aqueous vehicles include, without limitation, saline, buffered saline, 5% dextrose in water, and the like, and may further include one or more excipients, preservatives, solubilizers, buffering agents, albumin to prevent protein loss on vial surfaces, etc. Other suitable delivery vehicles include biocompatible solid or semi-solid matrices, including powdered bone, ceramics, biodegradable and non-biodegradable synthetic polymers, and natural polymers; tissue adhesives (e.g., fibrin-based); aqueous polymeric gels; liposomes; salves; creams; ointments; powders; and the like. These and other suitable vehicles are known in the art. Methods of formulation are well known in the art and are disclosed, for example, in *Remington: The Science and Practice of Pharmacy,* 20th ed., Gennaro et al., eds., Lippincott, Williams & Wilkins, Baltimore, 2000. In general, the composition is administered in an amount that produces a statistically significant beneficial effect, such as a statistically significant moderation or reversal of the progression or severity of a disease. The exact dose will be determined by the clinician according to accepted standards, taking into account the nature and severity of the condition to be treated, patient traits, etc. Determination of dose is within the level of ordinary skill in the art. Depending upon the route and method of administration, the protein may be administered in a single dose, as a prolonged infusion, or intermittently over an extended period. Intravenous administration will be by bolus injection or infusion over a typical period of one to several hours.

Sustained release formulations can be employed.

The invention is further illustrated by the following, non-limiting examples.

EXAMPLE 1

A vector encoding a heavy chain fusion partner (FusH) joined to an optimized t-PA leader (U.S. Pat. No. 5,641,655) and the extracellular domain (ECD) of zcytor7 (IL-20RA) (U.S. Pat. No. 5,945,511) was constructed. The DNA sequence encoding the fusion protein is shown in SEQ ID NO:11. The FusH sequence included a restriction enzyme site (SpeI), followed by sequences encoding the human Ig gamma1 hinge with a Cys to Ser mutation at Eu residue 220 (residue 103 of SEQ ID NO:1), two repeats of ($gly_3ser$) linker (SEQ ID NO:3), a thrombin cleavage motif, a human Ig gamma1 CH1 domain, and a 5-residue gamma1 hinge fragment. Component sequences were synthesized and assembled by polymerase chain reaction (PCR) using oligonucleotide primers and plasmid templates for zcytor7 and human Ig gamma1 for the protein domains. Primers for the zcytor7 sequence were oligonucleotides zc42398 (SEQ ID NO:13) and zc42651 (SEQ ID NO:14). Primers for the FusH domain were oligonucleotide zc42652 (SEQ ID NO:15) and two antisense oligonucleotides, zc42393 (SEQ ID NO:16) and zc42399 (SEQ ID NO:17). The resulting PCR products included 40 bp of flanking sequence to facilitate recombination in yeast as disclosed by Raymond et al., *Biotechniques* 26(1):134-138, 140-141, 1999; and U.S. Pat. No. 6,207,442. The PCR reactions were run in a 100 μl final volume containing 10 μl 10X Taq polymerase Reaction Buffer (Perkin Elmer), 8 μl of 2.5 mM dNTPs, 78 μl $dH_2O$, 2 μl each of 20 mM stock solutions of the two primers described above, and taq polymerase (2.5 units, Life Technologies). An equal volume of mineral oil was added, and the reaction mixture was heated to 94° C. for 2 minutes, followed by 25 cycles at 94° C. for 30 seconds, 45° C. for 30 seconds, 72° C. for 60 seconds followed by a 5-minute extension at 72° C. Ten μl of each of the 100 μl PCR reaction mixtures were run on a 1.0% agarose gel with 1× TBE buffer (45 mM tris-borate, 1 mM EDTA, pH8.3) for analysis. The remaining 90 μl of each reaction mixture was precipitated with the addition of 5 μl 1 M NaCl and 250 μl of absolute ethanol.

The plasmid pZMP21z, cut with BglII, was used for recombination with the PCR fragment. Plasmid pZMP21z was constructed from pZMP21 (deposited at the American Type Culture Collection, 10801 University Boulevard, Manassas, Va. 20110-2209, and designated No. PTA-5266) by replacement of the DHFR gene with the zeomycin resistance gene. Recombination of the PCR product into the linearized pZMP21z vector was performed essentially as disclosed by Raymond et al., ibid. One hundred microliters of competent *S. cerevisiae* strain SF838-9D (Rothman et al., *EMBO J.* 8:2057-2065, 1989) were combined with 10 μl of a 1:1 mixture of the PCR products for the zcytor7 and FusH domains and 200 ng of pZMP21z linearized with BglII and transferred to a 0.2-cm electroporation cuvette. The yeast/DNA mixtures were electropulsed at 0.75 kV (5 kV/cm), ∞ ohms, 25 μF in an electroporator (GENEPULSERII; BIO-RAD Laboratories, Hercules, Calif.). To each cuvette was added 600 μl of 1.2 M sorbitol, and the yeast was plated in two 300-μl aliquots onto two URA-D plates and incubated at 30° C. (URA-D contains 0.056% -Ura -Trp -Thr powder (made by combining 4.0 g L-adenine, 3.0 g L-arginine, 5.0 g L-aspartic acid, 2.0 g L-histidine, 6.0 g L-isoleucine, 8.0 g L-leucine, 4.0 g L-lysine, 2.0 g L-methionine, 6.0 g L-phenylalanine, 5.0 g L-serine, 5.0 g L-tyrosine, and 6.0 g L-valine), 0.67% yeast nitrogen base without amino acids, 2% D-glucose, 0.5% 200X tryptophan-threonine solution (3.0% L-threonine, 0.8% L-tryptophan in $H_2O$), 1.8% agar (BACTO, Difco Laboratories).) After about 48 hours, the Ura+ yeast transformants from a single plate were resuspended in 1 ml $H_2O$ and spun briefly to pellet the yeast cells. The cell pellet was resuspended in 1 ml of lysis buffer (2% TRITON X-100, 1% SDS, 100 mM NaCl, 10 mM Tris, pH 8.0, 1 mM EDTA). Five hundred microliters of the lysis mixture was added to a microcentrifuge tube containing 300 μl acid-washed glass beads and 200 μl phenol-chloroform mixture, vortexed for 1-minute intervals two or three times, followed by a 5-minute spin in a microcentrifuge at maximum speed. Three hundred microliters of the aqueous phase was transferred to a fresh tube, and the DNA was precipitated with 600 μl ethanol (EtOH), followed by centrifugation for 10 minutes at 4° C. The DNA pellet was resuspended in 10 μl $H_2O$.

Transformation of electrocompetent *E. coli* cells (DH10B, GibcoBRL) was done with 0.5-2 μl yeast DNA prep and 40 μl of DH10B cells. The cells were electropulsed at 1.7 kV, 25 μF and 400 ohms in an electroporator. Following electroporation, 1 ml SOC (2% BACTO Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was plated in 250-μl aliquots on four LB AMP plates (LB broth (Lennox), 1.8% BACTO Agar (Difco), 100 mg/L Ampicillin).

Individual *E. coli* clones harboring the correct construct were identified by restriction digest to verify the presence of the insert and to confirm that the various DNA sequences had been joined correctly to one another. The inserts of positive clones were subjected to DNA sequence analysis. Larger scale plasmid DNA was isolated using a commercially available plasmid DNA purification kit (QIAGEN Maxi kit; QIAGEN Inc., Valencia, Calif.) according to the manufacturer's instructions. The amino acid sequence of the fusion protein is shown in SEQ ID NO:12.

The zcytor7 ECD-FusH sequence was modified by the addition of an eight amino acid Gly-Ser linker (SEQ ID NO:2) between the zcytor7 ECD and the gamma1 hinge, and an eight amino acid histidine tag at the carboxyl terminus to aid in purification. The gly ser linker primers were zc43099 (SEQ ID NO:18) and zc43098 (SEQ ID NO:19). The his tag primers were zc43107 (SEQ ID NO:20) and zc43097 (SEQ ID NO:21). Double-stranded synthetic linker sequences were made by extension of oligonucleotide primers and added to the zcytor7 and FusH sequences by overlap PCR. Ten μl of each PCR product was used as template for the further levels of assembly. PCR reactions, yeast and *E. coli* transformations, and restriction mapping were carried out essentially as described above. The sequence of this construct is shown in SEQ ID NO:22.

EXAMPLE 2

The FusH sequence was mutagenized to modify the "ball-and-socket joint" for flexibility in the VH to CH1 interface as disclosed by Lesk and Chothia, *Nature* 335:188-90, 1988. The CH1 Phe residue, Eu number 150 (labeled 149 in Lesk and Chothia, ibid.; residue 33 of SEQ ID NO:1) was changed to Arg as shown in SEQ ID NO:24 and NO:25. The 5' end of the modified FusH sequence was synthesized by PCR using the His-tagged FusH sequence (Example 1) as a template with primer zc43107 (SEQ ID NO:20) and zc43146 (SEQ ID NO:26), and the 3' end with zc43145 (SEQ ID NO:27) and zc43098 (SEQ ID NO:19). The resulting two FusH fragments were assembled by overlap PCR with the primers zc43107 (SEQ ID NO:20) and zc43098 (SEQ ID NO:19). The assembled sequence, designated FusH F149R, was recombined with the zcytor7 fragment made with zc42398 and zc43097 by recombination in yeast. The sequence of this fusion is shown in SEQ ID NO:24 and NO:25.

EXAMPLE 3

A second FusH fusion protein, comprising the extracellular domain of zalpha11 (IL21R) (U.S. Patent Application Publication No. 20030148447), was made by insertion of the zalpha11 ECD and leader sequences into the vector pZMP21z (Example 1) with the FusH partner described in Example 2. Primers zc44173 (SEQ ID NO:28) and zc44819 (SEQ ID NO:29) were used to make the ECD coding sequence plus 40 bp extra for recombination via PCR with a previously constructed zalpha11 Ig fusion vector as a template. The FusH partner was modified for overlap with the zalpha11 ECD using primers zc44820 (SEQ ID NO:30) and zc43098 (SEQ ID NO:19), also with 40 bp of flanking sequence for recombination. The two fragments were co-electroporated into *S. cerevisiae* SF838-9D with pZMP21z that had been linearized with BglII as described for the previous expression vector using the procedures for PCR, electroporation, recovery of DNA from yeast cultures and screening disclosed above (Example 1). The DNA and amino acid sequences of the zalpha11-FusH polypeptide are shown in SEQ ID NOS:31 and 32.

EXAMPLE 4

A vector encoding a light chain fusion partner (FusL) joined to the leader and extracellular domain of DIRS1 (IL20RB) (WO 99/27103) was constructed. The FusL sequence included a restriction enzyme site (SpeI) and sequences encoding the human Ig gamma1 hinge, an eight-residue linker, a thrombin cleavage motif, and the human Ig kappa constant domain. The sequences were synthesized and assembled by PCR with oligonucleotide primers using existing plasmid templates for DIRS1 and human Ig kappa for the protein domains. The DIRS1 domain was made by PCR using oligonucleotide primers zc42409 (SEQ ID NO:33) and zc42449 (SEQ ID NO:34). The FusL domain was made by PCR with oligonucleotide primers zc42650 (SEQ ID NO:35), and zc42397 (SEQ ID NO:36). PCR, DNA analysis, transformation of yeast and *E. coli*, plasmid mapping, and sequencing were performed essentially as described for the construction of vectors in Example 1. The DNA and amino acid sequences for the fusion are shown in SEQ ID NO:37 and NO:38.

The plasmid pZMP31, which had been cut with BglII, was used for recombination with the PCR fragment. Plasmid pZMP31 was constructed from pZMP21 (deposited at the American Type Culture Collection, 10801 University Boulevard, Manassas, Va. 20110-2209, and designated No. PTA-5266) by the removal of the region from the truncated human CD8 alpha cDNA through the SV40 promoter/enhancer, leaving a single dicistronic cassette containing the polylinker followed by polio IRES, DHFR cDNA and SV40 poly A region. Following recombination in yeast, the resulting vector was designated DIRS1 C(FusL) pZMP31.

The DIRS1 ECD was modified by adding an eight amino acid (gly ser) linker (SEQ ID NO:2). The gly ser linker primers were zc43105 (SEQ ID NO:39) and zc43106 (SEQ ID NO:40). Double-stranded synthetic linker sequences were made by extension of oligonucleotide primers by PCR. To enable the recombination of this double-stranded oligonucleotide at one of the two SpeI sites of the pZMP31 vector, it was necessary to prepare several micrograms of a vector fragment that extended across that SpeI site. A 1.1 Kb PvuII to BsaBI fragment was isolated from the parent vector pZMP31. This fragment was isolated by agarose gel electrophoresis followed by purification using a commercially available gel purification kit (obtained from QIAGEN, Inc., Valencia, Calif.). The DNA fragments (three from the parental vector and the PCR product) were recombined in yeast to construct pDIRS1-FusL. The DNA and amino acid sequences of the DIRS1-FusL polypeptide are shown in SEQ ID NO:41 and SEQ ID NO:42.

EXAMPLE 5

A second FusL fusion protein was made with the extracellular domain of IL-2γC in the same format by insertion of the IL-2γC ECD sequence into the vector pZMP31 (described in Example 4) along with the FusL partner sequence described above, resulting in a γC-FusL fusion including an optimized t-PA leader. Primers zc40915 (SEQ ID NO:43) and zc44745 (SEQ ID NO:44) were used to make the ECD sequence with 40 bp overlaps for recombination, and primers zc44744 (SEQ ID NO:45) and zc42397 (SEQ ID NO:36) were used to make the FusL sequence by PCR. The two PCR products were inserted into BglII-cut pZMP31 as described above using recombination in yeast. The DNA and amino acid sequences of the IL-2γC-FusL polypeptide shown in SEQ ID NO:46 and NO:47.

EXAMPLE 6

Serum-free, suspension-adapted CHO DXB11 cells (Graf and Chasin, *Mol. Cell. Biol.* 2:93-96, 1982) were electroporated with pDIRS1-FusL plasmid (described in Example 4), the zcytor7-FusH plasmid (described in Example 2), and with both plasmids (to make the zcyto10 receptor heterodimer). The plasmids were linearized by digestion with PvuI, precipitated with sodium acetate and ethanol, then rinsed with 70% ethanol and dried. The pellets were resuspended at a concentration of 200 μg/100 μl per electroporation in serum- and protein-free medium (EX-CELL™ 325, JRH Biosciences, Lenexa, Ky.) supplemented with 4 mM L-Glutamine, 1% Hypoxanthine/Thymidine, 1% vitamins, and 1% Na pyruvate (media supplements purchased from INVITROGEN, Carlsbad, Calif.). Cells, growing at log phase, were pelleted and resuspended at $5\times10^6$ cells/800 μl per electroporation reaction. The electroporation was performed in an electroporator at 300 v and 950 μF in 4-mm cuvettes. The cells were suspended in 25 ml of the medium described above in 125-mL shake flasks and put on shakers in cell culture incubators at 37° C., at 80 rpm for 24 hours to recover. The cells were then pelleted and resuspended at $2.5\times10^5$ cells/mL in selective medium (EX-CELL™ 325 supplemented with 4 mM L-Glutamine, 1% vitamins, 1% Na Pyruvate and 200 μg/mL zeocin). Cell lines containing the DHFR gene were further cultured in increasing concentrations of methotrexate up to 1 μM once the cultures were capable of growing in the absence of hypoxanthine/thymidine supplementation. Once the cultures were growing actively in their respective selection media and the viability had increased to over 95%, cultures were established for harvest and analysis of protein. Cultures were seeded at $1\times10^6$ cells/mL at 25 mL in shake flasks, and allowed to grow for 48 hours, then harvested. The supernatants were filtered through 0.22 µm filters and purified by IMAC (Immobilized Metal Affinity Chromatography). The crude supernatants and the purified proteins were analyzed by SDS PAGE, Western blot, ELISA, and B cell activity assay.

Cells transformed with the FusH or FusL constructs only or cotransformed with both were analyzed by SDS PAGE and Western blot for expression, secretion into the medium, and assembly. Western blots were performed on 30-µl samples of conditioned medium and lysates from cells derived from an equivalent volume of culture. Duplicate blots were reacted with antibodies to each chain. The standard was zcytor7 Ig (the zcytor7 ECD joined to a human Ig gamma1 Fc fusion partner). Zcytor7-FusH protein was detected only in the lysate in the FusH homodimer cells (transformed with FusH construct only), indicating a lack of secretion of the FusH homodimer alone. The heterodimeric protein was detected in the conditioned medium as well as in the lysate of the heterodimer cell line (transformed with both FusH and FusL constructs). FusL was detected only in the conditioned medium in both the FusL homodimer and the heterodimer cell lines, indicating good secretion of the FusL subunit both alone and when assembled with the FusH. Purified protein was analyzed for information about assembly of the two subunits. Coomassie blue stained SDS PAGE of purified zcytor7 ECD-FusH/DIRS1 ECD-FusL heterodimer, both reduced and nonreduced, demonstrated the presence of the disulfide-bonded heterodimer.

EXAMPLE 7

Serum-free, suspension-adapted CHO DXB11 cells were electroporated with the IL-2γC-FusL plasmid (described in Example 5), the zalpha11-FusH plasmid (described in Example 3), and both plasmids (to make the IL-21 receptor heterodimer).

The plasmids were linearized by digestion with PvuI, precipitated with sodium acetate and ethanol, then rinsed with 70% ethanol and dried. The pellets were resuspended at a concentration of 200 µg/100 µl per electroporation in serum- and protein-free medium (EX-CELL™ 325, JRH Biosciences, Lenexa, KN) supplemented with 4 mM L-Glutamine, 1% Hypoxanthine/Thymidine, 1% vitamins and 1% Na pyruvate (supplements from INVITROGEN, Carlsbad, Calif.). Cells, growing at log phase, were pelleted and resuspended at $5\times10^6$ cells/800 µl per electroporation reaction. The electroporation was performed in an electroporator at 300 v and 950 µF in 4-mm cuvettes. The cells were suspended in 25 ml of the medium described above in 125-mL shake flasks and put on shakers in cell culture incubators at 37° C., at 80 rpm for 24 hours to recover. The cells were then pelleted and resuspended at $2.5\times10^5$ cells/mL in selective medium (EX-CELL™ 325 supplemented with 4 mM L-Glutamine, 1% vitamins, 1% Na Pyruvate and 200 µg/mL zeocin). Cell lines containing the DHFR gene were further cultured in increasing concentrations of methotrexate up to 1µM once the cultures were capable of growing in the absence of hypoxanthine/thymidine supplementation. Once the cultures were growing actively in their respective selection media and the viability had increased to over 95%, cultures were established for harvest and analysis of protein. Cultures were seeded at $1\times10^6$ cells/mL at 25 mL in shake flasks, and allowed to grow for 48 hours, then harvested. The supernatants were filtered through 0.22 µm filters and purified by IMAC. The crude supernatants and the purified proteins were analyzed by SDS PAGE, Western blot, ELISA, and B-cell activity assay.

A B-cell proliferation assay was performed with murine B-cells (Parrish-Novak et al, *Nature* 408:57-63, 2000) comparing inhibition mediated by soluble IL-21 receptor (Fc fusion heterodimer ("IL-21R Fc")) generated by purification with two epitope tags with the zalpha11 ECD FusH/γC FusL heterodimer purified by IMAC chromatography alone. The assay measured inhibition of uptake of [$^3$ H]thymidine by murine CD43 B cells treated with 2 µg/ml anti-CD40, 100 ng/ml murine IL-21, and varying concentrations of IL-21 receptor (Fc fusion heterodimer or FusH/FusL heterodimer). The activity of the FusH/FusL heterodimer was shown to be approximately equivalent to that of the purified Fc fusion heterodimer.

A cell-based inhibition assay was performed to compare the activities of the soluble Fc fusion to the the FusH/FusL form of the heterodimer. Fixed amounts of IL-21 were preincubated with a concentration series of each heterodimer. BaF3 cells (Palacios and Steinmetz, *Cell* 41: 727-734, 1985; Mathey-Prevot et al., *Mol. Cell. Biol.* 6: 4133-4135, 1986) transformed with IL-21R heterodimer constructs were incubated in a 96-well plate (VIEWPLATE; PerkinElmer, Wellesley, Mass.) for 48 hours at 37° C. and 6% $CO_2$ in IL-3-depleted medium containing the test mixture of soluble receptor heterodimer and IL-21 at a series of ratios from 0.4:1 up to 100:1. Cell growth was measured with 20 µl indicator dye (ALAMARBLUE®; Trek Diagnostic Systems, Cleveland, Ohio) per well. Fluorescence was read in microplate spectrofluorometer (GEMINI EM; Molecular Devices Corporation, Sunnyvale, Calif.) at an excitation wavelength of 530 nm and an emission wavelength of 590 nm. Results were normalized for the activity of IL21 on Baf3/IL21R cells. The activities of the two heterodimers were the same on a molar basis.

We claim:

1. A dimeric protein consisting of a first polypeptide fusion disulfide bonded to a second polypeptide fusion, wherein said first polypeptide fusion consists of, from amino terminus to carboxyl terminus, P1-L1-D1-$(P2)_n$, wherein said second polypeptide fusion consists of, from amino terminus to carboxyl terminus, P3-L2-D2, and wherein:

P1 is a first non-immunoglobulin polypeptide;

L1 is a first polypeptide linker consisting of from 18 to 32 amino acid residues, wherein x of said residues are cysteine residues;

P2 is a linking polypeptide consisting of from 1 to 29 amino acid residues, wherein at least one of said residues is a cysteine residue;

n is 0 or 1;

P3 is a second non-immunoglobulin polypeptide different from P1;

L2 is a second polypeptide linker consisting of from 18 to 32 amino acid residues, wherein y of said residues are cysteine residues;

D1 and D2 are dimerizing domains capable of dimerizing with each other, wherein D1 and D2 are respectively selected from the following dimerizing domain pairs:

(a) an immunoglobulin CH1 domain and an immunoglobulin light chain constant domain;

(b) a TCR Cα domain and a TCR Cβ domain;

(c) a TCR Cβ domain and a TCR Cα domain;

(d) an MHC class I $\alpha_3$ domain and a β2-microglobulin;

(e) a β2-microglobulin and an MHC class I $\alpha_3$ domain;

(f) an MHC class II $\alpha_2$ domain and an MHC class II $\beta_2$ domain; and (g) an MHC class II $\beta_2$ domain and an MHC class II $\alpha_2$ domain;

each of P1 and P3 is an extracellular domain of a cell-surface receptor requiring, in its native state, dimerization in order to initiate intracellular signal transduction;

each of x and y is an integer from 1 to 8; and x=y.

2. The dimeric protein of claim 1 wherein n=1.

3. The dimeric protein of claim 1 wherein x=2 and y=2.

4. The dimeric protein of claim 1, wherein each of P1 and P3 is an extracellular domain of a human cell-surface receptor.

5. The dimeric protein of claim 1, wherein each of P1 and P3 is not a member of the immunoglobulin superfamily.

6. The dimeric protein of claim 1 wherein each of P1 and P3 is individually selected from the group consisting of IL-17R, IL-20RA, IL-20RB, IL-21R, IL-28RA, IL-31RA, CRF2-4, and γC.

7. The dimeric protein of claim 1 wherein each of L1 and L2 contains exactly two cysteine residues.

8. The dimeric protein of claim 1 wherein each of L1 and L2 comprises an immunoglobulin hinge variant wherein the cysteine residue corresponding to residue 103 of SEQ ID NO:1 is replaced by serine.

9. The dimeric protein of claim 1 wherein each of L1 and L2 comprises a human γ1 hinge wherein the cysteine residue corresponding to residue 103 of SEQ ID NO:1 is replaced by serine.

10. The dimeric protein of claim 1 wherein each of L1 and L2 consists of 18 amino acid residues.

11. The dimeric protein of claim 1 wherein each of L1 and L2 comprises a plurality of glycine residues.

12. The dimeric protein of claim 1 wherein each of L1 and L2 comprises a plurality of serine residues.

13. The dimeric protein of claim 1 wherein each of L1 and L2 comprises [Gly-Ser-Gly-Ser]$_a$ (SEQ ID NO:2), wherein a is 1 or 2; or [Gly-Gly-Gly-Ser]$_b$ (SEQ ID NO:3), wherein b is 1 or 2.

14. The dimeric protein of claim 1 wherein each of L1 and L2 comprises a proteolytic cleavage site.

15. The dimeric protein of claim 1 wherein:

D1 is an immunoglobulin CH1 domain; and

D2 is an immunoglobulin κ light chain constant domain or immunoglobulin λ light chain constant domain.

16. The dimeric protein of claim 15 wherein D2 is an immunoglobulin κ light chain constant domain.

17. The dimeric protein of claim 1 wherein:

a) one of P1 and P3 is an IL-20RA extracellular domain and the other of P1 and P3 is an IL-20RB extracellular domain;

b) one of P1 and P3 is an IL-22RA1 extracellular domain and the other of P1 and P3 is an IL-20RB extracellular domain;

c) one of P1 and P3 is an IL-21R extracellular domain and the other of P1 and P3 is an IL-2 receptor γ common extracellular domain; or d) one P1 and P3 is a PDGF α receptor extracellular domain and the other of P1 and P3 is a PDGF β receptor extracellular domain.

18. A polypeptide fusion consisting of, from amino terminus to carboxyl terminus, P1-L-D1-(P2)$_n$, wherein:

P1 is a non-immunoglobulin polypeptide, wherein said non-immunoglobulin polypeptide is an extracellular domain of a cell-surface receptor requiring, in its native state, dimerization in order to initiate intracellular signal transduction;

L is a polypeptide linker consisting of from 18 to 32 amino acid residues, wherein from 1 to 8 of said residues are cysteine residues;

D1 is a dimerizing domain selected from the group consisting of an immunoglobulin CH1 domain, a T-cell receptor Cα domain, a T-cell receptor Cβ domain, a major histocompatibility complex class I α3 domain, β2-microglobulin, a major histocompatibility complex class II α2 domain, and a major histocompatibility complex class II β2 domain;

P2 is a linking polypeptide consisting of from 1 to 29 amino acid residues, wherein at least one of said residues is a cysteine residue; and n is 0 or 1.

19. The polypeptide fusion of claim 18 wherein D1 is an immunoglobulin γ1 CH1 domain.

20. The polypeptide fusion of claim 19 wherein the γ1 CH1 domain is a human γ1 CH1 domain.

21. The polypeptide fusion of claim 18 wherein P2 is a portion of an immunoglobulin hinge comprising a cysteine residue.

22. The polypeptide fusion of claim 18 wherein n is 1 and P2 consists of from 5 to 15 amino acid residues.

23. The polypeptide fusion of claim 18 wherein n is 1 and P2 contains exactly one cysteine residue.

24. A polypeptide fusion consisting of, from amino terminus to carboxyl terminus, P3-L-D2, wherein:

P3 is a non-immunoglobulin polypeptide, said non-immunoglobulin polypeptide being an extracellular domain of a cell-surface receptor requiring, in its native state, dimerization in order to initiate intracellular signal transduction;

L is a polypeptide linker consisting of from 18 to 32 amino acid residues, wherein from 1 to 8 of said residues are cysteine residues; and D2 is a dimerizing domain selected from the group consisting of an immunoglobulin light chain constant domain, a T-cell receptor Cα domain, a T-cell receptor Cβ domain, a major histocompatibility complex class I α3 domain, β2-microglobulin, a major histocompatibility complex class II α2 domain, and a major histocompatibility complex class II β2 domain.

* * * * *

SEQUENCE LISTING

```
<160> NUMBER OF SEQ ID NOS: 63

<210> SEQ ID NO 1
<211> LENGTH: 330
<212> TYPE: PRT
<213> ORGANISM: Homo sapiens

<400> SEQUENCE: 1

Ala Ser Thr Lys Gly Pro Ser Val Phe Pro Leu Ala Pro Ser Ser Lys
 1               5                  10                  15
```

-continued

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 2
<211> LENGTH: 4
<212> TYPE: PRT
<213> ORGANISM: Artificial Sequence
<220> FEATURE:
<223> OTHER INFORMATION: peptide linker

<400> SEQUENCE: 2

Gly Ser Gly Ser
 1


<210> SEQ ID NO 3
<211> LENGTH: 4
<212> TYPE: PRT
<213> ORGANISM: Artificial Sequence
```

-continued

<220> FEATURE:
<223> OTHER INFORMATION: peptide linker

<400> SEQUENCE: 3

Gly Gly Gly Ser
1

<210> SEQ ID NO 4
<211> LENGTH: 5
<212> TYPE: PRT
<213> ORGANISM: Artificial Sequence
<220> FEATURE:
<223> OTHER INFORMATION: enterokinase cleavage site

<400> SEQUENCE: 4

Asp Asp Asp Asp Lys
1 5

<210> SEQ ID NO 5
<211> LENGTH: 4
<212> TYPE: PRT
<213> ORGANISM: Artificial Sequence
<220> FEATURE:
<223> OTHER INFORMATION: factor Xa cleavage site

<400> SEQUENCE: 5

Ile Glu Gly Arg
1

<210> SEQ ID NO 6
<211> LENGTH: 8
<212> TYPE: PRT
<213> ORGANISM: Artificial Sequence
<220> FEATURE:
<223> OTHER INFORMATION: rhinovirus C3 protease cleavage site

<400> SEQUENCE: 6

Leu Glu Val Leu Phe Gln Gly Pro
1 5

<210> SEQ ID NO 7
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: VARIANT
<222> LOCATION: (2)...(2)
<223> OTHER INFORMATION: Xaa = any amino acid
<220> FEATURE:
<221> NAME/KEY: VARIANT
<222> LOCATION: (3)...(3)
<223> OTHER INFORMATION: Xaa = Lys or Arg

<400> SEQUENCE: 7

Arg Xaa Xaa Arg
1

<210> SEQ ID NO 8
<211> LENGTH: 7
<212> TYPE: PRT
<213> ORGANISM: Artificial Sequence
<220> FEATURE:
<223> OTHER INFORMATION: renin cleavage site

<400> SEQUENCE: 8

Pro Phe His Leu Leu Val Tyr

-continued

```
 1               5


<210> SEQ ID NO 9
<211> LENGTH: 5
<212> TYPE: PRT
<213> ORGANISM: Artificial Sequence
<220> FEATURE:
<223> OTHER INFORMATION: collagenase cleavage site
<220> FEATURE:
<221> NAME/KEY: VARIANT
<222> LOCATION: (1)...(5)
<223> OTHER INFORMATION: Xaa = Any Amino Acid

<400> SEQUENCE: 9

Pro Xaa Gly Pro Xaa
 1               5


<210> SEQ ID NO 10
<211> LENGTH: 4
<212> TYPE: PRT
<213> ORGANISM: Artificial Sequence
<220> FEATURE:
<223> OTHER INFORMATION: caspase-3 cleavage site

<400> SEQUENCE: 10

Asp Glu Val Asp
 1


<210> SEQ ID NO 11
<211> LENGTH: 1155
<212> TYPE: DNA
<213> ORGANISM: Artificial Sequence
<220> FEATURE:
<223> OTHER INFORMATION: DNA encoding fusion protein
<220> FEATURE:
<221> NAME/KEY: CDS
<222> LOCATION: (1)...(1155)

<400> SEQUENCE: 11

atg gat gca atg aag aga ggg ctc tgc tgt gtg ctg ctg ctg tgt ggc       48
Met Asp Ala Met Lys Arg Gly Leu Cys Cys Val Leu Leu Leu Cys Gly
 1               5                  10                  15

gcc gtc ttc gtt tcg ctc agc cag gaa atc cat gcc gag ttg aga cgc       96
Ala Val Phe Val Ser Leu Ser Gln Glu Ile His Ala Glu Leu Arg Arg
            20                  25                  30

ttc cgt aga gca gtt ccc tgt gtc tct ggt ggt ttg cct aaa cct gca      144
Phe Arg Arg Ala Val Pro Cys Val Ser Gly Gly Leu Pro Lys Pro Ala
        35                  40                  45

aac atc acc ttc tta tcc atc aac atg aag aat gtc cta caa tgg act      192
Asn Ile Thr Phe Leu Ser Ile Asn Met Lys Asn Val Leu Gln Trp Thr
    50                  55                  60

cca cca gag ggt ctt caa gga gtt aaa gtt act tac act gtg cag tat      240
Pro Pro Glu Gly Leu Gln Gly Val Lys Val Thr Tyr Thr Val Gln Tyr
 65                  70                  75                  80

ttc ata tat ggg caa aag aaa tgg ctg aat aaa tca gaa tgc aga aat      288
Phe Ile Tyr Gly Gln Lys Lys Trp Leu Asn Lys Ser Glu Cys Arg Asn
                85                  90                  95

atc aat aga acc tac tgt gat ctt tct gct gaa act tct gac tac gaa      336
Ile Asn Arg Thr Tyr Cys Asp Leu Ser Ala Glu Thr Ser Asp Tyr Glu
            100                 105                 110

cac cag tat tat gcc aaa gtt aag gcc att tgg gga aca aag tgt tcc      384
His Gln Tyr Tyr Ala Lys Val Lys Ala Ile Trp Gly Thr Lys Cys Ser
        115                 120                 125

aaa tgg gct gaa agt gga cgg ttc tat cct ttt tta gaa aca caa att      432
Lys Trp Ala Glu Ser Gly Arg Phe Tyr Pro Phe Leu Glu Thr Gln Ile
```

-continued

```
    130                 135                 140

ggc cca cca gag gtg gca ctg act aca gat gag aag tcc att tct gtt      480
Gly Pro Pro Glu Val Ala Leu Thr Thr Asp Glu Lys Ser Ile Ser Val
145                 150                 155                 160

gtc ctg aca gct cca gag aag tgg aag aga aat cca gaa gac ctt cct      528
Val Leu Thr Ala Pro Glu Lys Trp Lys Arg Asn Pro Glu Asp Leu Pro
                165                 170                 175

gtt tcc atg caa caa ata tac tcc aat ctg aag tat aac gtg tct gtg      576
Val Ser Met Gln Gln Ile Tyr Ser Asn Leu Lys Tyr Asn Val Ser Val
            180                 185                 190

ttg aat act aaa tca aac aga acg tgg tcc cag tgt gtg acc aac cac      624
Leu Asn Thr Lys Ser Asn Arg Thr Trp Ser Gln Cys Val Thr Asn His
        195                 200                 205

acg ctg gtg ctc acc tgg ctg gag ccg aac act ctt tac tgc gta cac      672
Thr Leu Val Leu Thr Trp Leu Glu Pro Asn Thr Leu Tyr Cys Val His
    210                 215                 220

gtg gag tcc ttc gtc cca ggg ccc cct cgc cgt gct cag cct tct gag      720
Val Glu Ser Phe Val Pro Gly Pro Pro Arg Arg Ala Gln Pro Ser Glu
225                 230                 235                 240

aag cag tgt gcc agg act ttg aaa gat caa tca tca gag act agt gaa      768
Lys Gln Cys Ala Arg Thr Leu Lys Asp Gln Ser Ser Glu Thr Ser Glu
                245                 250                 255

cca aag tcc agc gac aaa act cac aca tgc cca ccg tgc cca ggt gga      816
Pro Lys Ser Ser Asp Lys Thr His Thr Cys Pro Pro Cys Pro Gly Gly
            260                 265                 270

gga tcc ggc ggt gga tca ctg gtt ccg cgt tcc acc aag ggc cca tcg      864
Gly Ser Gly Gly Gly Ser Leu Val Pro Arg Ser Thr Lys Gly Pro Ser
        275                 280                 285

gtc ttc ccc ctg gca ccc tcc tcc aag agc acc tct ggg ggc aca gcg      912
Val Phe Pro Leu Ala Pro Ser Ser Lys Ser Thr Ser Gly Gly Thr Ala
    290                 295                 300

gcc ctg ggc tgc ctg gtc aag gac tac ttc ccc gaa ccg gtg acg gtg      960
Ala Leu Gly Cys Leu Val Lys Asp Tyr Phe Pro Glu Pro Val Thr Val
305                 310                 315                 320

tcg tgg aac tca ggc gcc ctg acc agc ggc gtg cac acc ttc ccg gct     1008
Ser Trp Asn Ser Gly Ala Leu Thr Ser Gly Val His Thr Phe Pro Ala
                325                 330                 335

gtc cta cag tcc tca gga ctc tac tcc ctc agc agc gtg gtg acc gtg     1056
Val Leu Gln Ser Ser Gly Leu Tyr Ser Leu Ser Ser Val Val Thr Val
            340                 345                 350

ccc tcc agc agc ttg ggc acc cag acc tac atc tgc aac gtg aat cac     1104
Pro Ser Ser Ser Leu Gly Thr Gln Thr Tyr Ile Cys Asn Val Asn His
        355                 360                 365

aag ccc agc aac acc aag gtg gac aag aaa gtt gag ccc aaa tct tgt     1152
Lys Pro Ser Asn Thr Lys Val Asp Lys Lys Val Glu Pro Lys Ser Cys
    370                 375                 380

taa                                                                 1155
 *


<210> SEQ ID NO 12
<211> LENGTH: 384
<212> TYPE: PRT
<213> ORGANISM: Artificial Sequence
<220> FEATURE:
<223> OTHER INFORMATION: fusion protein

<400> SEQUENCE: 12

Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
```

-continued

```
            20                  25                  30

Phe Arg Arg Ala Val Pro Cys Val Ser Gly Gly Leu Pro Lys Pro Ala
        35                  40                  45

Asn Ile Thr Phe Leu Ser Ile Asn Met Lys Asn Val Leu Gln Trp Thr
    50                  55                  60

Pro Pro Glu Gly Leu Gln Gly Val Lys Val Thr Tyr Thr Val Gln Tyr
65                  70                  75                  80

Phe Ile Tyr Gly Gln Lys Lys Trp Leu Asn Lys Ser Glu Cys Arg Asn
                85                  90                  95

Ile Asn Arg Thr Tyr Cys Asp Leu Ser Ala Glu Thr Ser Asp Tyr Glu
            100                 105                 110

His Gln Tyr Tyr Ala Lys Val Lys Ala Ile Trp Gly Thr Lys Cys Ser
        115                 120                 125

Lys Trp Ala Glu Ser Gly Arg Phe Tyr Pro Phe Leu Glu Thr Gln Ile
    130                 135                 140

Gly Pro Pro Glu Val Ala Leu Thr Thr Asp Glu Lys Ser Ile Ser Val
145                 150                 155                 160

Val Leu Thr Ala Pro Glu Lys Trp Lys Arg Asn Pro Glu Asp Leu Pro
                165                 170                 175

Val Ser Met Gln Gln Ile Tyr Ser Asn Leu Lys Tyr Asn Val Ser Val
            180                 185                 190

Leu Asn Thr Lys Ser Asn Arg Thr Trp Ser Gln Cys Val Thr Asn His
        195                 200                 205

Thr Leu Val Leu Thr Trp Leu Glu Pro Asn Thr Leu Tyr Cys Val His
    210                 215                 220

Val Glu Ser Phe Val Pro Gly Pro Pro Arg Arg Ala Gln Pro Ser Glu
225                 230                 235                 240

Lys Gln Cys Ala Arg Thr Leu Lys Asp Gln Ser Ser Glu Thr Ser Glu
                245                 250                 255

Pro Lys Ser Ser Asp Lys Thr His Thr Cys Pro Pro Cys Pro Gly Gly
            260                 265                 270

Gly Ser Gly Gly Gly Ser Leu Val Pro Arg Ser Thr Lys Gly Pro Ser
        275                 280                 285

Val Phe Pro Leu Ala Pro Ser Ser Lys Ser Thr Ser Gly Gly Thr Ala
    290                 295                 300

Ala Leu Gly Cys Leu Val Lys Asp Tyr Phe Pro Glu Pro Val Thr Val
305                 310                 315                 320

Ser Trp Asn Ser Gly Ala Leu Thr Ser Gly Val His Thr Phe Pro Ala
                325                 330                 335

Val Leu Gln Ser Ser Gly Leu Tyr Ser Leu Ser Ser Val Val Thr Val
            340                 345                 350

Pro Ser Ser Ser Leu Gly Thr Gln Thr Tyr Ile Cys Asn Val Asn His
        355                 360                 365

Lys Pro Ser Asn Thr Lys Val Asp Lys Lys Val Glu Pro Lys Ser Cys
    370                 375                 380

<210> SEQ ID NO 13
<211> LENGTH: 60
<212> TYPE: DNA
<213> ORGANISM: Artificial Sequence
<220> FEATURE:
<223> OTHER INFORMATION: oligonucleotide primer ZC42398

<400> SEQUENCE: 13

cagccaggaa atccatgccg agttgagacg cttccgtaga gcagttccct gtgtctctgg     60
```

-continued

<210> SEQ ID NO 14
<211> LENGTH: 75
<212> TYPE: DNA
<213> ORGANISM: Artificial Sequence
<220> FEATURE:
<223> OTHER INFORMATION: oligonucleotide primer ZC42651

<400> SEQUENCE: 14
acctgggcac ggtgggcatg tgtgagtttt gtcgctggac tttggttcac tagtctctga 60
tgattgatct ttcaa 75

<210> SEQ ID NO 15
<211> LENGTH: 75
<212> TYPE: DNA
<213> ORGANISM: Artificial Sequence
<220> FEATURE:
<223> OTHER INFORMATION: oligonucleotide primer ZC42652

<400> SEQUENCE: 15
acatgcccac cgtgcccagg tggaggatcc ggcggtggat cactggttcc gcgttccacc 60
aagggcccat cggtc 75

<210> SEQ ID NO 16
<211> LENGTH: 47
<212> TYPE: DNA
<213> ORGANISM: Artificial Sequence
<220> FEATURE:
<223> OTHER INFORMATION: oligonucleotide primer ZC42393

<400> SEQUENCE: 16
gatttaacaa gatttgggct caactttctt gtccaccttg gtgttgc 47

<210> SEQ ID NO 17
<211> LENGTH: 59
<212> TYPE: DNA
<213> ORGANISM: Artificial Sequence
<220> FEATURE:
<223> OTHER INFORMATION: oligonucleotide primer ZC42399

<400> SEQUENCE: 17
gggtacaacc ccagagctgt tttaaggcgc gcctctagat ttaacaagat ttgggctca 59

<210> SEQ ID NO 18
<211> LENGTH: 63
<212> TYPE: DNA
<213> ORGANISM: Artificial Sequence
<220> FEATURE:
<223> OTHER INFORMATION: oligonucleotide primer ZC43099

<400> SEQUENCE: 18
caacaccaag gtggacaaga aagttgagcc caaatcttgt caccatcacc accatcacca 60
tca 63

<210> SEQ ID NO 19
<211> LENGTH: 63
<212> TYPE: DNA
<213> ORGANISM: Artificial Sequence
<220> FEATURE:
<223> OTHER INFORMATION: oligonucleotide primer ZC43098

<400> SEQUENCE: 19
tacaacccca gagctgtttt aaggcgcgcc tctagattta gtgatggtga tggtggtgat 60

-continued

```
ggt                                                                    63


<210> SEQ ID NO 20
<211> LENGTH: 63
<212> TYPE: DNA
<213> ORGANISM: Artificial Sequence
<220> FEATURE:
<223> OTHER INFORMATION: oligonucleotide primer ZC43107

<400> SEQUENCE: 20

gaagcagtgt gccaggactt tgaaagatca atcatcagag ggatccggtt cgggttcggg     60

ttc                                                                    63


<210> SEQ ID NO 21
<211> LENGTH: 66
<212> TYPE: DNA
<213> ORGANISM: Artificial Sequence
<220> FEATURE:
<223> OTHER INFORMATION: oligonucleotide primer ZC43097

<400> SEQUENCE: 21

agttttgtcg ctggactttg gttcactagt tgatctgggc tccgaacccg aacccgaacc     60

ggatcc                                                                 66


<210> SEQ ID NO 22
<211> LENGTH: 1215
<212> TYPE: DNA
<213> ORGANISM: Artificial Sequence
<220> FEATURE:
<223> OTHER INFORMATION: DNA encoding fusion protein
<220> FEATURE:
<221> NAME/KEY: CDS
<222> LOCATION: (1)...(1215)

<400> SEQUENCE: 22

atg gat gca atg aag aga ggg ctc tgc tgt gtg ctg ctg ctg tgt ggc       48
Met Asp Ala Met Lys Arg Gly Leu Cys Cys Val Leu Leu Leu Cys Gly
 1               5                  10                  15

gcc gtc ttc gtt tcg ctc agc cag gaa atc cat gcc gag ttg aga cgc       96
Ala Val Phe Val Ser Leu Ser Gln Glu Ile His Ala Glu Leu Arg Arg
            20                  25                  30

ttc cgt aga gca gtt ccc tgt gtc tct ggt ggt ttg cct aaa cct gca      144
Phe Arg Arg Ala Val Pro Cys Val Ser Gly Gly Leu Pro Lys Pro Ala
        35                  40                  45

aac atc acc ttc tta tcc atc aac atg aag aat gtc cta caa tgg act      192
Asn Ile Thr Phe Leu Ser Ile Asn Met Lys Asn Val Leu Gln Trp Thr
    50                  55                  60

cca cca gag ggt ctt caa gga gtt aaa gtt act tac act gtg cag tat      240
Pro Pro Glu Gly Leu Gln Gly Val Lys Val Thr Tyr Thr Val Gln Tyr
 65                  70                  75                  80

ttc ata tat ggg caa aag aaa tgg ctg aat aaa tca gaa tgc aga aat      288
Phe Ile Tyr Gly Gln Lys Lys Trp Leu Asn Lys Ser Glu Cys Arg Asn
                85                  90                  95

atc aat aga acc tac tgt gat ctt tct gct gaa act tct gac tac gaa      336
Ile Asn Arg Thr Tyr Cys Asp Leu Ser Ala Glu Thr Ser Asp Tyr Glu
            100                 105                 110

cac cag tat tat gcc aaa gtt aag gcc att tgg gga aca aag tgt tcc      384
His Gln Tyr Tyr Ala Lys Val Lys Ala Ile Trp Gly Thr Lys Cys Ser
        115                 120                 125

aaa tgg gct gaa agt gga cgg ttc tat cct ttt tta gaa aca caa att      432
Lys Trp Ala Glu Ser Gly Arg Phe Tyr Pro Phe Leu Glu Thr Gln Ile
    130                 135                 140
```

-continued

```
ggc cca cca gag gtg gca ctg act aca gat gag aag tcc att tct gtt      480
Gly Pro Pro Glu Val Ala Leu Thr Thr Asp Glu Lys Ser Ile Ser Val
145                 150                 155                 160

gtc ctg aca gct cca gag aag tgg aag aga aat cca gaa gac ctt cct      528
Val Leu Thr Ala Pro Glu Lys Trp Lys Arg Asn Pro Glu Asp Leu Pro
                165                 170                 175

gtt tcc atg caa caa ata tac tcc aat ctg aag tat aac gtg tct gtg      576
Val Ser Met Gln Gln Ile Tyr Ser Asn Leu Lys Tyr Asn Val Ser Val
            180                 185                 190

ttg aat act aaa tca aac aga acg tgg tcc cag tgt gtg acc aac cac      624
Leu Asn Thr Lys Ser Asn Arg Thr Trp Ser Gln Cys Val Thr Asn His
        195                 200                 205

acg ctg gtg ctc acc tgg ctg gag ccg aac act ctt tac tgc gta cac      672
Thr Leu Val Leu Thr Trp Leu Glu Pro Asn Thr Leu Tyr Cys Val His
    210                 215                 220

gtg gag tcc ttc gtc cca ggg ccc cct cgc cgt gct cag cct tct gag      720
Val Glu Ser Phe Val Pro Gly Pro Pro Arg Arg Ala Gln Pro Ser Glu
225                 230                 235                 240

aag cag tgt gcc agg act ttg aaa gat caa tca tca gag gga tcc ggt      768
Lys Gln Cys Ala Arg Thr Leu Lys Asp Gln Ser Ser Glu Gly Ser Gly
                245                 250                 255

tcg ggt tcg ggt tcg gag ccc aga tca act agt gaa cca aag tcc agc      816
Ser Gly Ser Gly Ser Glu Pro Arg Ser Thr Ser Glu Pro Lys Ser Ser
            260                 265                 270

gac aaa act cac aca tgc cca ccg tgc cca ggt gga gga tcc ggc ggt      864
Asp Lys Thr His Thr Cys Pro Pro Cys Pro Gly Gly Gly Ser Gly Gly
        275                 280                 285

gga tca ctg gtt ccg cgt tcc acc aag ggc cca tcg gtc ttc ccc ctg      912
Gly Ser Leu Val Pro Arg Ser Thr Lys Gly Pro Ser Val Phe Pro Leu
    290                 295                 300

gca ccc tcc tcc aag agc acc tct ggg ggc aca gcg gcc ctg ggc tgc      960
Ala Pro Ser Ser Lys Ser Thr Ser Gly Gly Thr Ala Ala Leu Gly Cys
305                 310                 315                 320

ctg gtc aag gac tac ttc ccc gaa ccg gtg acg gtg tcg tgg aac tca     1008
Leu Val Lys Asp Tyr Phe Pro Glu Pro Val Thr Val Ser Trp Asn Ser
                325                 330                 335

ggc gcc ctg acc agc ggc gtg cac acc ttc ccg gct gtc cta cag tcc     1056
Gly Ala Leu Thr Ser Gly Val His Thr Phe Pro Ala Val Leu Gln Ser
            340                 345                 350

tca gga ctc tac tcc ctc agc agc gtg gtg acc gtg ccc tcc agc agc     1104
Ser Gly Leu Tyr Ser Leu Ser Ser Val Val Thr Val Pro Ser Ser Ser
        355                 360                 365

ttg ggc acc cag acc tac atc tgc aac gtg aat cac aag ccc agc aac     1152
Leu Gly Thr Gln Thr Tyr Ile Cys Asn Val Asn His Lys Pro Ser Asn
    370                 375                 380

acc aag gtg gac aag aaa gtt gag ccc aaa tct tgt cac cat cac cac     1200
Thr Lys Val Asp Lys Lys Val Glu Pro Lys Ser Cys His His His His
385                 390                 395                 400

cat cac cat cac taa                                                 1215
His His His His  *


<210> SEQ ID NO 23
<211> LENGTH: 404
<212> TYPE: PRT
<213> ORGANISM: Artificial Sequence
<220> FEATURE:
<223> OTHER INFORMATION: fusion protein

<400> SEQUENCE: 23

Met Asp Ala Met Lys Arg Gly Leu Cys Cys Val Leu Leu Leu Cys Gly
 1               5                  10                  15
```

-continued

```
Ala Val Phe Val Ser Leu Ser Gln Glu Ile His Ala Glu Leu Arg Arg
            20                  25                  30

Phe Arg Arg Ala Val Pro Cys Val Ser Gly Gly Leu Pro Lys Pro Ala
        35                  40                  45

Asn Ile Thr Phe Leu Ser Ile Asn Met Lys Asn Val Leu Gln Trp Thr
    50                  55                  60

Pro Pro Glu Gly Leu Gln Gly Val Lys Val Thr Tyr Thr Val Gln Tyr
65                  70                  75                  80

Phe Ile Tyr Gly Gln Lys Lys Trp Leu Asn Lys Ser Glu Cys Arg Asn
                85                  90                  95

Ile Asn Arg Thr Tyr Cys Asp Leu Ser Ala Glu Thr Ser Asp Tyr Glu
            100                 105                 110

His Gln Tyr Tyr Ala Lys Val Lys Ala Ile Trp Gly Thr Lys Cys Ser
        115                 120                 125

Lys Trp Ala Glu Ser Gly Arg Phe Tyr Pro Phe Leu Glu Thr Gln Ile
    130                 135                 140

Gly Pro Pro Glu Val Ala Leu Thr Thr Asp Glu Lys Ser Ile Ser Val
145                 150                 155                 160

Val Leu Thr Ala Pro Glu Lys Trp Lys Arg Asn Pro Glu Asp Leu Pro
                165                 170                 175

Val Ser Met Gln Gln Ile Tyr Ser Asn Leu Lys Tyr Asn Val Ser Val
            180                 185                 190

Leu Asn Thr Lys Ser Asn Arg Thr Trp Ser Gln Cys Val Thr Asn His
        195                 200                 205

Thr Leu Val Leu Thr Trp Leu Glu Pro Asn Thr Leu Tyr Cys Val His
    210                 215                 220

Val Glu Ser Phe Val Pro Gly Pro Pro Arg Arg Ala Gln Pro Ser Glu
225                 230                 235                 240

Lys Gln Cys Ala Arg Thr Leu Lys Asp Gln Ser Ser Glu Gly Ser Gly
                245                 250                 255

Ser Gly Ser Gly Ser Glu Pro Arg Ser Thr Ser Glu Pro Lys Ser Ser
            260                 265                 270

Asp Lys Thr His Thr Cys Pro Pro Cys Pro Gly Gly Gly Ser Gly Gly
        275                 280                 285

Gly Ser Leu Val Pro Arg Ser Thr Lys Gly Pro Ser Val Phe Pro Leu
    290                 295                 300

Ala Pro Ser Ser Lys Ser Thr Ser Gly Gly Thr Ala Ala Leu Gly Cys
305                 310                 315                 320

Leu Val Lys Asp Tyr Phe Pro Glu Pro Val Thr Val Ser Trp Asn Ser
                325                 330                 335

Gly Ala Leu Thr Ser Gly Val His Thr Phe Pro Ala Val Leu Gln Ser
            340                 345                 350

Ser Gly Leu Tyr Ser Leu Ser Ser Val Val Thr Val Pro Ser Ser Ser
        355                 360                 365

Leu Gly Thr Gln Thr Tyr Ile Cys Asn Val Asn His Lys Pro Ser Asn
    370                 375                 380

Thr Lys Val Asp Lys Lys Val Glu Pro Lys Ser Cys His His His His
385                 390                 395                 400

His His His His
```

<210> SEQ ID NO 24
<211> LENGTH: 1215
<212> TYPE: DNA

```
<213> ORGANISM: Artificial Sequence
<220> FEATURE:
<223> OTHER INFORMATION: DNA encoding fusion protein
<220> FEATURE:
<221> NAME/KEY: CDS
<222> LOCATION: (1)...(1215)

<400> SEQUENCE: 24

atg gat gca atg aag aga ggg ctc tgc tgt gtg ctg ctg ctg tgt ggc      48
Met Asp Ala Met Lys Arg Gly Leu Cys Cys Val Leu Leu Leu Cys Gly
 1               5                  10                  15

gcc gtc ttc gtt tcg ctc agc cag gaa atc cat gcc gag ttg aga cgc      96
Ala Val Phe Val Ser Leu Ser Gln Glu Ile His Ala Glu Leu Arg Arg
            20                  25                  30

ttc cgt aga gca gtt ccc tgt gtc tct ggt ggt ttg cct aaa cct gca     144
Phe Arg Arg Ala Val Pro Cys Val Ser Gly Gly Leu Pro Lys Pro Ala
        35                  40                  45

aac atc acc ttc tta tcc atc aac atg aag aat gtc cta caa tgg act     192
Asn Ile Thr Phe Leu Ser Ile Asn Met Lys Asn Val Leu Gln Trp Thr
    50                  55                  60

cca cca gag ggt ctt caa gga gtt aaa gtt act tac act gtg cag tat     240
Pro Pro Glu Gly Leu Gln Gly Val Lys Val Thr Tyr Thr Val Gln Tyr
 65                  70                  75                  80

ttc ata tat ggg caa aag aaa tgg ctg aat aaa tca gaa tgc aga aat     288
Phe Ile Tyr Gly Gln Lys Lys Trp Leu Asn Lys Ser Glu Cys Arg Asn
                85                  90                  95

atc aat aga acc tac tgt gat ctt tct gct gaa act tct gac tac gaa     336
Ile Asn Arg Thr Tyr Cys Asp Leu Ser Ala Glu Thr Ser Asp Tyr Glu
            100                 105                 110

cac cag tat tat gcc aaa gtt aag gcc att tgg gga aca aag tgt tcc     384
His Gln Tyr Tyr Ala Lys Val Lys Ala Ile Trp Gly Thr Lys Cys Ser
        115                 120                 125

aaa tgg gct gaa agt gga cgg ttc tat cct ttt tta gaa aca caa att     432
Lys Trp Ala Glu Ser Gly Arg Phe Tyr Pro Phe Leu Glu Thr Gln Ile
    130                 135                 140

ggc cca cca gag gtg gca ctg act aca gat gag aag tcc att tct gtt     480
Gly Pro Pro Glu Val Ala Leu Thr Thr Asp Glu Lys Ser Ile Ser Val
145                 150                 155                 160

gtc ctg aca gct cca gag aag tgg aag aga aat cca gaa gac ctt cct     528
Val Leu Thr Ala Pro Glu Lys Trp Lys Arg Asn Pro Glu Asp Leu Pro
                165                 170                 175

gtt tcc atg caa caa ata tac tcc aat ctg aag tat aac gtg tct gtg     576
Val Ser Met Gln Gln Ile Tyr Ser Asn Leu Lys Tyr Asn Val Ser Val
            180                 185                 190

ttg aat act aaa tca aac aga acg tgg tcc cag tgt gtg acc aac cac     624
Leu Asn Thr Lys Ser Asn Arg Thr Trp Ser Gln Cys Val Thr Asn His
        195                 200                 205

acg ctg gtg ctc acc tgg ctg gag ccg aac act ctt tac tgc gta cac     672
Thr Leu Val Leu Thr Trp Leu Glu Pro Asn Thr Leu Tyr Cys Val His
    210                 215                 220

gtg gag tcc ttc gtc cca ggg ccc cct cgc cgt gct cag cct tct gag     720
Val Glu Ser Phe Val Pro Gly Pro Pro Arg Arg Ala Gln Pro Ser Glu
225                 230                 235                 240

aag cag tgt gcc agg act ttg aaa gat caa tca tca gag gga tcc ggt     768
Lys Gln Cys Ala Arg Thr Leu Lys Asp Gln Ser Ser Glu Gly Ser Gly
                245                 250                 255

tcg ggt tcg ggt tcg gag ccc aga tca act agt gaa cca aag tcc agc     816
Ser Gly Ser Gly Ser Glu Pro Arg Ser Thr Ser Glu Pro Lys Ser Ser
            260                 265                 270

gac aaa act cac aca tgc cca ccg tgc cca ggt gga gga tcc ggc ggt     864
Asp Lys Thr His Thr Cys Pro Pro Cys Pro Gly Gly Gly Ser Gly Gly
```

-continued

```
        275                 280                 285

gga tca ctg gtt ccg cgt tcc acc aag ggc cca tcg gtc ttc ccc ctg      912
Gly Ser Leu Val Pro Arg Ser Thr Lys Gly Pro Ser Val Phe Pro Leu
    290                 295                 300

gca ccc tcc tcc aag agc acc tct ggg ggc aca gcg gcc ctg ggc tgc      960
Ala Pro Ser Ser Lys Ser Thr Ser Gly Gly Thr Ala Ala Leu Gly Cys
305                 310                 315                 320

ctg gtc aag gac tac cgt ccc gaa ccg gtg acg gtg tcg tgg aac tca     1008
Leu Val Lys Asp Tyr Arg Pro Glu Pro Val Thr Val Ser Trp Asn Ser
                325                 330                 335

ggc gcc ctg acc agc ggc gtg cac acc ttc ccg gct gtc cta cag tcc     1056
Gly Ala Leu Thr Ser Gly Val His Thr Phe Pro Ala Val Leu Gln Ser
            340                 345                 350

tca gga ctc tac tcc ctc agc agc gtg gtg acc gtg ccc tcc agc agc     1104
Ser Gly Leu Tyr Ser Leu Ser Ser Val Val Thr Val Pro Ser Ser Ser
        355                 360                 365

ttg ggc acc cag acc tac atc tgc aac gtg aat cac aag ccc agc aac     1152
Leu Gly Thr Gln Thr Tyr Ile Cys Asn Val Asn His Lys Pro Ser Asn
    370                 375                 380

acc aag gtg gac aag aaa gtt gag ccc aaa tct tgt cac cat cac cac     1200
Thr Lys Val Asp Lys Lys Val Glu Pro Lys Ser Cys His His His His
385                 390                 395                 400

cat cac cat cac taa                                                 1215
His His His His  *


<210> SEQ ID NO 25
<211> LENGTH: 404
<212> TYPE: PRT
<213> ORGANISM: Artificial Sequence
<220> FEATURE:
<223> OTHER INFORMATION: fusion protein

<400> SEQUENCE: 25

Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
            20                  25                  30

Phe Arg Arg Ala Val Pro Cys Val Ser Gly Gly Leu Pro Lys Pro Ala
        35                  40                  45

Asn Ile Thr Phe Leu Ser Ile Asn Met Lys Asn Val Leu Gln Trp Thr
    50                  55                  60

Pro Pro Glu Gly Leu Gln Gly Val Lys Val Thr Tyr Thr Val Gln Tyr
65                  70                  75                  80

Phe Ile Tyr Gly Gln Lys Lys Trp Leu Asn Lys Ser Glu Cys Arg Asn
                85                  90                  95

Ile Asn Arg Thr Tyr Cys Asp Leu Ser Ala Glu Thr Ser Asp Tyr Glu
            100                 105                 110

His Gln Tyr Tyr Ala Lys Val Lys Ala Ile Trp Gly Thr Lys Cys Ser
        115                 120                 125

Lys Trp Ala Glu Ser Gly Arg Phe Tyr Pro Phe Leu Glu Thr Gln Ile
    130                 135                 140

Gly Pro Pro Glu Val Ala Leu Thr Thr Asp Glu Lys Ser Ile Ser Val
145                 150                 155                 160

Val Leu Thr Ala Pro Glu Lys Trp Lys Arg Asn Pro Glu Asp Leu Pro
                165                 170                 175

Val Ser Met Gln Gln Ile Tyr Ser Asn Leu Lys Tyr Asn Val Ser Val
            180                 185                 190
```

```
Leu Asn Thr Lys Ser Asn Arg Thr Trp Ser Gln Cys Val Thr Asn His
        195                 200                 205

Thr Leu Val Leu Thr Trp Leu Glu Pro Asn Thr Leu Tyr Cys Val His
    210                 215                 220

Val Glu Ser Phe Val Pro Gly Pro Pro Arg Arg Ala Gln Pro Ser Glu
225                 230                 235                 240

Lys Gln Cys Ala Arg Thr Leu Lys Asp Gln Ser Ser Glu Gly Ser Gly
                245                 250                 255

Ser Gly Ser Gly Ser Glu Pro Arg Ser Thr Ser Glu Pro Lys Ser Ser
            260                 265                 270

Asp Lys Thr His Thr Cys Pro Pro Cys Pro Gly Gly Gly Ser Gly Gly
        275                 280                 285

Gly Ser Leu Val Pro Arg Ser Thr Lys Gly Pro Ser Val Phe Pro Leu
    290                 295                 300

Ala Pro Ser Ser Lys Ser Thr Ser Gly Gly Thr Ala Ala Leu Gly Cys
305                 310                 315                 320

Leu Val Lys Asp Tyr Arg Pro Glu Pro Val Thr Val Ser Trp Asn Ser
                325                 330                 335

Gly Ala Leu Thr Ser Gly Val His Thr Phe Pro Ala Val Leu Gln Ser
            340                 345                 350

Ser Gly Leu Tyr Ser Leu Ser Ser Val Val Thr Val Pro Ser Ser Ser
        355                 360                 365

Leu Gly Thr Gln Thr Tyr Ile Cys Asn Val Asn His Lys Pro Ser Asn
    370                 375                 380

Thr Lys Val Asp Lys Lys Val Glu Pro Lys Ser Cys His His His His
385                 390                 395                 400

His His His His


<210> SEQ ID NO 26
<211> LENGTH: 27
<212> TYPE: DNA
<213> ORGANISM: Artificial Sequence
<220> FEATURE:
<223> OTHER INFORMATION: oligonucleotide linker ZC43146

<400> SEQUENCE: 26

caccggttcg ggacggtagt ccttgac                                          27


<210> SEQ ID NO 27
<211> LENGTH: 27
<212> TYPE: DNA
<213> ORGANISM: Artificial Sequence
<220> FEATURE:
<223> OTHER INFORMATION: oligonucleotide linker ZC43145

<400> SEQUENCE: 27

gtcaaggact accgtcccga accggtg                                          27


<210> SEQ ID NO 28
<211> LENGTH: 67
<212> TYPE: DNA
<213> ORGANISM: Artificial Sequence
<220> FEATURE:
<223> OTHER INFORMATION: oligonucleotide linker ZC44173

<400> SEQUENCE: 28

tgcctttctc tccacaggtg tccagggaat tcatataggc cggccaccat gccgcgtggc      60

tgggccg                                                                67
```

-continued

<210> SEQ ID NO 29
<211> LENGTH: 45
<212> TYPE: DNA
<213> ORGANISM: Artificial Sequence
<220> FEATURE:
<223> OTHER INFORMATION: oligonucleotide linker ZC44819

<400> SEQUENCE: 29
gctggacttt ggttcactag tcgaacccga acccgaaccg gatcc 45

<210> SEQ ID NO 30
<211> LENGTH: 45
<212> TYPE: DNA
<213> ORGANISM: Artificial Sequence
<220> FEATURE:
<223> OTHER INFORMATION: oligonucleotide linker ZC44820

<400> SEQUENCE: 30
ggatccggtt cgggttcggg ttcgactagt gaaccaaagt ccagc 45

<210> SEQ ID NO 31
<211> LENGTH: 1155
<212> TYPE: DNA
<213> ORGANISM: Artificial Sequence
<220> FEATURE:
<223> OTHER INFORMATION: DNA encoding fusion protein
<220> FEATURE:
<221> NAME/KEY: CDS
<222> LOCATION: (1)...(1155)

<400> SEQUENCE: 31

```
atg ccg cgt ggc tgg gcc gcc ccc ttg ctc ctg ctg ctg ctc cag gga      48
Met Pro Arg Gly Trp Ala Ala Pro Leu Leu Leu Leu Leu Leu Gln Gly
 1               5                  10                  15

ggc tgg ggc tgc ccc gac ctc gtc tgc tac acc gat tac ctc cag acg      96
Gly Trp Gly Cys Pro Asp Leu Val Cys Tyr Thr Asp Tyr Leu Gln Thr
            20                  25                  30

gtc atc tgc atc ctg gaa atg tgg aac ctc cac ccc agc acg ctc acc     144
Val Ile Cys Ile Leu Glu Met Trp Asn Leu His Pro Ser Thr Leu Thr
        35                  40                  45

ctt acc tgg caa gac cag tat gaa gag ctg aag gac gag gcc acc tcc     192
Leu Thr Trp Gln Asp Gln Tyr Glu Glu Leu Lys Asp Glu Ala Thr Ser
    50                  55                  60

tgc agc ctc cac agg tcg gcc cac aat gcc acg cat gcc acc tac acc     240
Cys Ser Leu His Arg Ser Ala His Asn Ala Thr His Ala Thr Tyr Thr
65                  70                  75                  80

tgc cac atg gat gta ttc cac ttc atg gcc gac gac att ttc agt gtc     288
Cys His Met Asp Val Phe His Phe Met Ala Asp Asp Ile Phe Ser Val
                85                  90                  95

aac atc aca gac cag tct ggc aac tac tcc cag gag tgt ggc agc ttt     336
Asn Ile Thr Asp Gln Ser Gly Asn Tyr Ser Gln Glu Cys Gly Ser Phe
            100                 105                 110

ctc ctg gct gag agc atc aag ccg gct ccc cct ttc aac gtg act gtg     384
Leu Leu Ala Glu Ser Ile Lys Pro Ala Pro Pro Phe Asn Val Thr Val
        115                 120                 125

acc ttc tca gga cag tat aat atc tcc tgg cgc tca gat tac gaa gac     432
Thr Phe Ser Gly Gln Tyr Asn Ile Ser Trp Arg Ser Asp Tyr Glu Asp
    130                 135                 140

cct gcc ttc tac atg ctg aag ggc aag ctt cag tat gag ctg cag tac     480
Pro Ala Phe Tyr Met Leu Lys Gly Lys Leu Gln Tyr Glu Leu Gln Tyr
145                 150                 155                 160

agg aac cgg gga gac ccc tgg gct gtg agt ccg agg aga aag ctg atc     528
Arg Asn Arg Gly Asp Pro Trp Ala Val Ser Pro Arg Arg Lys Leu Ile
```

-continued

```
                165                 170                 175

tca gtg gac tca aga agt gtc tcc ctc ctc ccc ctg gag ttc cgc aaa      576
Ser Val Asp Ser Arg Ser Val Ser Leu Leu Pro Leu Glu Phe Arg Lys
            180                 185                 190

gac tcg agc tat gag ctg cag gtg cgg gca ggg ccc atg cct ggc tcc      624
Asp Ser Ser Tyr Glu Leu Gln Val Arg Ala Gly Pro Met Pro Gly Ser
        195                 200                 205

tcc tac cag ggg acc tgg agt gaa tgg agt gac ccg gtc atc ttt cag      672
Ser Tyr Gln Gly Thr Trp Ser Glu Trp Ser Asp Pro Val Ile Phe Gln
    210                 215                 220

acc cag tca gag gag tta aag gaa ggc tgg aac cct cac gga tcc ggt      720
Thr Gln Ser Glu Glu Leu Lys Glu Gly Trp Asn Pro His Gly Ser Gly
225                 230                 235                 240

tcg ggt tcg ggt tcg act agt gaa cca aag tcc agc gac aaa act cac      768
Ser Gly Ser Gly Ser Thr Ser Glu Pro Lys Ser Ser Asp Lys Thr His
                245                 250                 255

aca tgc cca ccg tgc cca ggt gga gga tcc ggc ggt gga tca ctg gtt      816
Thr Cys Pro Pro Cys Pro Gly Gly Gly Ser Gly Gly Gly Ser Leu Val
            260                 265                 270

ccg cgt tcc acc aag ggc cca tcg gtc ttc ccc ctg gca ccc tcc tcc      864
Pro Arg Ser Thr Lys Gly Pro Ser Val Phe Pro Leu Ala Pro Ser Ser
        275                 280                 285

aag agc acc tct ggg ggc aca gcg gcc ctg ggc tgc ctg gtc aag gac      912
Lys Ser Thr Ser Gly Gly Thr Ala Ala Leu Gly Cys Leu Val Lys Asp
    290                 295                 300

tac cgt ccc gaa ccg gtg acg gtg tcg tgg aac tca ggc gcc ctg acc      960
Tyr Arg Pro Glu Pro Val Thr Val Ser Trp Asn Ser Gly Ala Leu Thr
305                 310                 315                 320

agc ggc gtg cac acc ttc ccg gct gtc cta cag tcc tca gga ctc tac     1008
Ser Gly Val His Thr Phe Pro Ala Val Leu Gln Ser Ser Gly Leu Tyr
                325                 330                 335

tcc ctc agc agc gtg gtg acc gtg ccc tcc agc agc ttg ggc acc cag     1056
Ser Leu Ser Ser Val Val Thr Val Pro Ser Ser Ser Leu Gly Thr Gln
            340                 345                 350

acc tac atc tgc aac gtg aat cac aag ccc agc aac acc aag gtg gac     1104
Thr Tyr Ile Cys Asn Val Asn His Lys Pro Ser Asn Thr Lys Val Asp
        355                 360                 365

aag aaa gtt gag ccc aaa tct tgt cac cat cac cac cat cac cat cac     1152
Lys Lys Val Glu Pro Lys Ser Cys His His His His His His His His
    370                 375                 380

taa                                                                 1155
 *


<210> SEQ ID NO 32
<211> LENGTH: 384
<212> TYPE: PRT
<213> ORGANISM: Artificial Sequence
<220> FEATURE:
<223> OTHER INFORMATION: fusion protein

<400> SEQUENCE: 32

Met Pro Arg Gly Trp Ala Ala Pro Leu Leu Leu Leu Leu Leu Gln Gly
 1               5                  10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60
```

-continued

```
Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Gly Ser Gly
225                 230                 235                 240

Ser Gly Ser Gly Ser Thr Ser Glu Pro Lys Ser Ser Asp Lys Thr His
                245                 250                 255

Thr Cys Pro Pro Cys Pro Gly Gly Gly Ser Gly Gly Gly Ser Leu Val
            260                 265                 270

Pro Arg Ser Thr Lys Gly Pro Ser Val Phe Pro Leu Ala Pro Ser Ser
        275                 280                 285

Lys Ser Thr Ser Gly Gly Thr Ala Ala Leu Gly Cys Leu Val Lys Asp
    290                 295                 300

Tyr Arg Pro Glu Pro Val Thr Val Ser Trp Asn Ser Gly Ala Leu Thr
305                 310                 315                 320

Ser Gly Val His Thr Phe Pro Ala Val Leu Gln Ser Ser Gly Leu Tyr
                325                 330                 335

Ser Leu Ser Ser Val Val Thr Val Pro Ser Ser Ser Leu Gly Thr Gln
            340                 345                 350

Thr Tyr Ile Cys Asn Val Asn His Lys Pro Ser Asn Thr Lys Val Asp
        355                 360                 365

Lys Lys Val Glu Pro Lys Ser Cys His His His His His His His His
    370                 375                 380


<210> SEQ ID NO 33
<211> LENGTH: 63
<212> TYPE: DNA
<213> ORGANISM: Artificial Sequence
<220> FEATURE:
<223> OTHER INFORMATION: oligonucleotide linker ZC42409

<400> SEQUENCE: 33

tccacaggtg tccagggaat tcatataggc cggccaccat gcagactttc acaatggttc      60

tag                                                                    63


<210> SEQ ID NO 34
<211> LENGTH: 78
<212> TYPE: DNA
<213> ORGANISM: Artificial Sequence
```

-continued

```
<220> FEATURE:
<223> OTHER INFORMATION: oligonucleotide linker ZC42449

<400> SEQUENCE: 34

acctgggcac ggtgggcatg tgtgagtttt gtcgctagat ttgggctcac tagtggcctc     60

tccttgcacc tccacaca                                                   78


<210> SEQ ID NO 35
<211> LENGTH: 78
<212> TYPE: DNA
<213> ORGANISM: Artificial Sequence
<220> FEATURE:
<223> OTHER INFORMATION: oligonucleotide linker ZC42650

<400> SEQUENCE: 35

acatgcccac cgtgcccagg tggaggatcc ggcggtggat cactggttcc gcgtcgaact     60

gtggctgcac catctgtc                                                   78


<210> SEQ ID NO 36
<211> LENGTH: 61
<212> TYPE: DNA
<213> ORGANISM: Artificial Sequence
<220> FEATURE:
<223> OTHER INFORMATION: oligonucleotide linker ZC42397

<400> SEQUENCE: 36

tacaacccca gagctgtttt aaggcgcgcc tctagattta acactctccc ctgttgaagc     60

t                                                                     61


<210> SEQ ID NO 37
<211> LENGTH: 1101
<212> TYPE: DNA
<213> ORGANISM: Artificial Sequence
<220> FEATURE:
<223> OTHER INFORMATION: DNA encoding fusion protein
<220> FEATURE:
<221> NAME/KEY: CDS
<222> LOCATION: (1)...(1101)

<400> SEQUENCE: 37

atg cag act ttc aca atg gtt cta gaa gaa atc tgg aca agt ctt ttc       48
Met Gln Thr Phe Thr Met Val Leu Glu Glu Ile Trp Thr Ser Leu Phe
 1               5                  10                  15

atg tgg ttt ttc tac gca ttg att cca tgt ttg ctc aca gat gaa gtg       96
Met Trp Phe Phe Tyr Ala Leu Ile Pro Cys Leu Leu Thr Asp Glu Val
            20                  25                  30

gcc att ctg cct gcc cct cag aac ctc tct gta ctc tca acc aac atg      144
Ala Ile Leu Pro Ala Pro Gln Asn Leu Ser Val Leu Ser Thr Asn Met
        35                  40                  45

aag cat ctc ttg atg tgg agc cca gtg atc gcg cct gga gaa aca gtg      192
Lys His Leu Leu Met Trp Ser Pro Val Ile Ala Pro Gly Glu Thr Val
    50                  55                  60

tac tat tct gtc gaa tac cag ggg gag tac gag agc ctg tac acg agc      240
Tyr Tyr Ser Val Glu Tyr Gln Gly Glu Tyr Glu Ser Leu Tyr Thr Ser
 65                  70                  75                  80

cac atc tgg atc ccc agc agc tgg tgc tca ctc act gaa ggt cct gag      288
His Ile Trp Ile Pro Ser Ser Trp Cys Ser Leu Thr Glu Gly Pro Glu
                 85                  90                  95

tgt gat gtc act gat gac atc acg gcc act gtg cca tac aac ctt cgt      336
Cys Asp Val Thr Asp Asp Ile Thr Ala Thr Val Pro Tyr Asn Leu Arg
            100                 105                 110

gtc agg gcc aca ttg ggc tca cag acc tca gcc tgg agc atc ctg aag      384
```

-continued

```
Val Arg Ala Thr Leu Gly Ser Gln Thr Ser Ala Trp Ser Ile Leu Lys
        115                 120                 125

cat ccc ttt aat aga aac tca acc atc ctt acc cga cct ggg atg gag      432
His Pro Phe Asn Arg Asn Ser Thr Ile Leu Thr Arg Pro Gly Met Glu
    130                 135                 140

atc acc aaa gat ggc ttc cac ctg gtt att gag ctg gag gac ctg ggg      480
Ile Thr Lys Asp Gly Phe His Leu Val Ile Glu Leu Glu Asp Leu Gly
145                 150                 155                 160

ccc cag ttt gag ttc ctt gtg gcc tac tgg agg agg gag cct ggt gcc      528
Pro Gln Phe Glu Phe Leu Val Ala Tyr Trp Arg Arg Glu Pro Gly Ala
                165                 170                 175

gag gaa cat gtc aaa atg gtg agg agt ggg ggt att cca gtg cac cta      576
Glu Glu His Val Lys Met Val Arg Ser Gly Gly Ile Pro Val His Leu
            180                 185                 190

gaa acc atg gag cca ggg gct gca tac tgt gtg aag gcc cag aca ttc      624
Glu Thr Met Glu Pro Gly Ala Ala Tyr Cys Val Lys Ala Gln Thr Phe
        195                 200                 205

gtg aag gcc att ggg agg tac agc gcc ttc agc cag aca gaa tgt gtg      672
Val Lys Ala Ile Gly Arg Tyr Ser Ala Phe Ser Gln Thr Glu Cys Val
    210                 215                 220

gag gtg caa gga gag gcc act agt gag ccc aaa tct agc gac aaa act      720
Glu Val Gln Gly Glu Ala Thr Ser Glu Pro Lys Ser Ser Asp Lys Thr
225                 230                 235                 240

cac aca tgc cca ccg tgc cca ggt gga gga tcc ggc ggt gga tca ctg      768
His Thr Cys Pro Pro Cys Pro Gly Gly Gly Ser Gly Gly Gly Ser Leu
                245                 250                 255

gtt ccg cgt cga act gtg gct gca cca tct gtc ttc atc ttc ccg cca      816
Val Pro Arg Arg Thr Val Ala Ala Pro Ser Val Phe Ile Phe Pro Pro
            260                 265                 270

tct gat gag cag ttg aaa tct ggt acc gcc tct gtt gtg tgc ctg ctg      864
Ser Asp Glu Gln Leu Lys Ser Gly Thr Ala Ser Val Val Cys Leu Leu
        275                 280                 285

aat aac ttc tat ccc aga gag gcc aaa gta cag tgg aag gtg gat aac      912
Asn Asn Phe Tyr Pro Arg Glu Ala Lys Val Gln Trp Lys Val Asp Asn
    290                 295                 300

gcc ctc caa tcg ggt aac tcc cag gag agt gtc aca gag cag gac agc      960
Ala Leu Gln Ser Gly Asn Ser Gln Glu Ser Val Thr Glu Gln Asp Ser
305                 310                 315                 320

aag gac agc acc tac agc ctc agc agc acc ctg acg ctg agc aaa gca     1008
Lys Asp Ser Thr Tyr Ser Leu Ser Ser Thr Leu Thr Leu Ser Lys Ala
                325                 330                 335

gac tac gag aaa cac aaa gtc tac gcc tgc gaa gtc acc cat cag ggc     1056
Asp Tyr Glu Lys His Lys Val Tyr Ala Cys Glu Val Thr His Gln Gly
            340                 345                 350

ctg agc tcg ccc gtc aca aag agc ttc aac agg gga gag tgt taa         1101
Leu Ser Ser Pro Val Thr Lys Ser Phe Asn Arg Gly Glu Cys  *
        355                 360                 365


<210> SEQ ID NO 38
<211> LENGTH: 366
<212> TYPE: PRT
<213> ORGANISM: Artificial Sequence
<220> FEATURE:
<223> OTHER INFORMATION: fusion protein

<400> SEQUENCE: 38

Met Gln Thr Phe Thr Met Val Leu Glu Glu Ile Trp Thr Ser Leu Phe
 1               5                  10                  15

Met Trp Phe Phe Tyr Ala Leu Ile Pro Cys Leu Leu Thr Asp Glu Val
            20                  25                  30
```

-continued

```
Ala Ile Leu Pro Ala Pro Gln Asn Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Glu Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140

Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Thr Ser Glu Pro Lys Ser Ser Asp Lys Thr
225                 230                 235                 240

His Thr Cys Pro Pro Cys Pro Gly Gly Gly Ser Gly Gly Gly Ser Leu
                245                 250                 255

Val Pro Arg Arg Thr Val Ala Ala Pro Ser Val Phe Ile Phe Pro Pro
            260                 265                 270

Ser Asp Glu Gln Leu Lys Ser Gly Thr Ala Ser Val Val Cys Leu Leu
        275                 280                 285

Asn Asn Phe Tyr Pro Arg Glu Ala Lys Val Gln Trp Lys Val Asp Asn
    290                 295                 300

Ala Leu Gln Ser Gly Asn Ser Gln Glu Ser Val Thr Glu Gln Asp Ser
305                 310                 315                 320

Lys Asp Ser Thr Tyr Ser Leu Ser Ser Thr Leu Thr Leu Ser Lys Ala
                325                 330                 335

Asp Tyr Glu Lys His Lys Val Tyr Ala Cys Glu Val Thr His Gln Gly
            340                 345                 350

Leu Ser Ser Pro Val Thr Lys Ser Phe Asn Arg Gly Glu Cys
        355                 360                 365
```

<210> SEQ ID NO 39
<211> LENGTH: 65
<212> TYPE: DNA
<213> ORGANISM: Artificial Sequence
<220> FEATURE:
<223> OTHER INFORMATION: oligonucleotide primer ZC43105

<400> SEQUENCE: 39

```
cttcagccag acagaatgtg tggaggtgca aggagaggcc ggatccggtt cgggttcggg     60

ttcga                                                                 65
```

<210> SEQ ID NO 40

-continued

```
<211> LENGTH: 65
<212> TYPE: DNA
<213> ORGANISM: Artificial Sequence
<220> FEATURE:
<223> OTHER INFORMATION: oligonucleotide primer ZC43106

<400> SEQUENCE: 40

ggcatgtgtg agttttgtcg ctagatttgg gctcactagt cgaacccgaa cccgaaccgg     60

atccg                                                                 65


<210> SEQ ID NO 41
<211> LENGTH: 1125
<212> TYPE: DNA
<213> ORGANISM: Artificial Sequence
<220> FEATURE:
<223> OTHER INFORMATION: DNA encoding fusion protein
<220> FEATURE:
<221> NAME/KEY: CDS
<222> LOCATION: (1)...(1125)

<400> SEQUENCE: 41

atg cag act ttc aca atg gtt cta gaa gaa atc tgg aca agt ctt ttc       48
Met Gln Thr Phe Thr Met Val Leu Glu Glu Ile Trp Thr Ser Leu Phe
 1               5                  10                  15

atg tgg ttt ttc tac gca ttg att cca tgt ttg ctc aca gat gaa gtg       96
Met Trp Phe Phe Tyr Ala Leu Ile Pro Cys Leu Leu Thr Asp Glu Val
            20                  25                  30

gcc att ctg cct gcc cct cag aac ctc tct gta ctc tca acc aac atg      144
Ala Ile Leu Pro Ala Pro Gln Asn Leu Ser Val Leu Ser Thr Asn Met
        35                  40                  45

aag cat ctc ttg atg tgg agc cca gtg atc gcg cct gga gaa aca gtg      192
Lys His Leu Leu Met Trp Ser Pro Val Ile Ala Pro Gly Glu Thr Val
    50                  55                  60

tac tat tct gtc gaa tac cag ggg gag tac gag agc ctg tac acg agc      240
Tyr Tyr Ser Val Glu Tyr Gln Gly Glu Tyr Glu Ser Leu Tyr Thr Ser
 65                  70                  75                  80

cac atc tgg atc ccc agc agc tgg tgc tca ctc act gaa ggt cct gag      288
His Ile Trp Ile Pro Ser Ser Trp Cys Ser Leu Thr Glu Gly Pro Glu
                85                  90                  95

tgt gat gtc act gat gac atc acg gcc act gtg cca tac aac ctt cgt      336
Cys Asp Val Thr Asp Asp Ile Thr Ala Thr Val Pro Tyr Asn Leu Arg
            100                 105                 110

gtc agg gcc aca ttg ggc tca cag acc tca gcc tgg agc atc ctg aag      384
Val Arg Ala Thr Leu Gly Ser Gln Thr Ser Ala Trp Ser Ile Leu Lys
        115                 120                 125

cat ccc ttt aat aga aac tca acc atc ctt acc cga cct ggg atg gag      432
His Pro Phe Asn Arg Asn Ser Thr Ile Leu Thr Arg Pro Gly Met Glu
    130                 135                 140

atc acc aaa gat ggc ttc cac ctg gtt att gag ctg gag gac ctg ggg      480
Ile Thr Lys Asp Gly Phe His Leu Val Ile Glu Leu Glu Asp Leu Gly
145                 150                 155                 160

ccc cag ttt gag ttc ctt gtg gcc tac tgg agg agg gag cct ggt gcc      528
Pro Gln Phe Glu Phe Leu Val Ala Tyr Trp Arg Arg Glu Pro Gly Ala
                165                 170                 175

gag gaa cat gtc aaa atg gtg agg agt ggg ggt att cca gtg cac cta      576
Glu Glu His Val Lys Met Val Arg Ser Gly Gly Ile Pro Val His Leu
            180                 185                 190

gaa acc atg gag cca ggg gct gca tac tgt gtg aag gcc cag aca ttc      624
Glu Thr Met Glu Pro Gly Ala Ala Tyr Cys Val Lys Ala Gln Thr Phe
        195                 200                 205

gtg aag gcc att ggg agg tac agc gcc ttc agc cag aca gaa tgt gtg      672
Val Lys Ala Ile Gly Arg Tyr Ser Ala Phe Ser Gln Thr Glu Cys Val
```

```
    210                 215                 220

gag gtg caa gga gag gcc gga tcc ggt tcg ggt tcg ggt tcg act agt      720
Glu Val Gln Gly Glu Ala Gly Ser Gly Ser Gly Ser Gly Ser Thr Ser
225                 230                 235                 240

gag ccc aaa tct agc gac aaa act cac aca tgc cca ccg tgc cca ggt      768
Glu Pro Lys Ser Ser Asp Lys Thr His Thr Cys Pro Pro Cys Pro Gly
                245                 250                 255

gga gga tcc ggc ggt gga tca ctg gtt ccg cgt cga act gtg gct gca      816
Gly Gly Ser Gly Gly Gly Ser Leu Val Pro Arg Arg Thr Val Ala Ala
            260                 265                 270

cca tct gtc ttc atc ttc ccg cca tct gat gag cag ttg aaa tct ggt      864
Pro Ser Val Phe Ile Phe Pro Pro Ser Asp Glu Gln Leu Lys Ser Gly
        275                 280                 285

acc gcc tct gtt gtg tgc ctg ctg aat aac ttc tat ccc aga gag gcc      912
Thr Ala Ser Val Val Cys Leu Leu Asn Asn Phe Tyr Pro Arg Glu Ala
    290                 295                 300

aaa gta cag tgg aag gtg gat aac gcc ctc caa tcg ggt aac tcc cag      960
Lys Val Gln Trp Lys Val Asp Asn Ala Leu Gln Ser Gly Asn Ser Gln
305                 310                 315                 320

gag agt gtc aca gag cag gac agc aag gac agc acc tac agc ctc agc     1008
Glu Ser Val Thr Glu Gln Asp Ser Lys Asp Ser Thr Tyr Ser Leu Ser
                325                 330                 335

agc acc ctg acg ctg agc aaa gca gac tac gag aaa cac aaa gtc tac     1056
Ser Thr Leu Thr Leu Ser Lys Ala Asp Tyr Glu Lys His Lys Val Tyr
            340                 345                 350

gcc tgc gaa gtc acc cat cag ggc ctg agc tcg ccc gtc aca aag agc     1104
Ala Cys Glu Val Thr His Gln Gly Leu Ser Ser Pro Val Thr Lys Ser
        355                 360                 365

ttc aac agg gga gag tgt taa                                         1125
Phe Asn Arg Gly Glu Cys  *
    370


<210> SEQ ID NO 42
<211> LENGTH: 374
<212> TYPE: PRT
<213> ORGANISM: Artificial Sequence
<220> FEATURE:
<223> OTHER INFORMATION: fusion protein

<400> SEQUENCE: 42

Met Gln Thr Phe Thr Met Val Leu Glu Glu Ile Trp Thr Ser Leu Phe
 1               5                  10                  15

Met Trp Phe Phe Tyr Ala Leu Ile Pro Cys Leu Leu Thr Asp Glu Val
            20                  25                  30

Ala Ile Leu Pro Ala Pro Gln Asn Leu Ser Val Leu Ser Thr Asn Met
        35                  40                  45

Lys His Leu Leu Met Trp Ser Pro Val Ile Ala Pro Gly Glu Thr Val
    50                  55                  60

Tyr Tyr Ser Val Glu Tyr Gln Gly Glu Tyr Glu Ser Leu Tyr Thr Ser
65                  70                  75                  80

His Ile Trp Ile Pro Ser Ser Trp Cys Ser Leu Thr Glu Gly Pro Glu
                85                  90                  95

Cys Asp Val Thr Asp Asp Ile Thr Ala Thr Val Pro Tyr Asn Leu Arg
            100                 105                 110

Val Arg Ala Thr Leu Gly Ser Gln Thr Ser Ala Trp Ser Ile Leu Lys
        115                 120                 125

His Pro Phe Asn Arg Asn Ser Thr Ile Leu Thr Arg Pro Gly Met Glu
    130                 135                 140
```

-continued

```
Ile Thr Lys Asp Gly Phe His Leu Val Ile Glu Leu Glu Asp Leu Gly
145                 150                 155                 160

Pro Gln Phe Glu Phe Leu Val Ala Tyr Trp Arg Arg Glu Pro Gly Ala
                165                 170                 175

Glu Glu His Val Lys Met Val Arg Ser Gly Gly Ile Pro Val His Leu
            180                 185                 190

Glu Thr Met Glu Pro Gly Ala Ala Tyr Cys Val Lys Ala Gln Thr Phe
        195                 200                 205

Val Lys Ala Ile Gly Arg Tyr Ser Ala Phe Ser Gln Thr Glu Cys Val
    210                 215                 220

Glu Val Gln Gly Glu Ala Gly Ser Gly Ser Gly Ser Gly Ser Thr Ser
225                 230                 235                 240

Glu Pro Lys Ser Ser Asp Lys Thr His Thr Cys Pro Pro Cys Pro Gly
                245                 250                 255

Gly Gly Ser Gly Gly Gly Ser Leu Val Pro Arg Arg Thr Val Ala Ala
            260                 265                 270

Pro Ser Val Phe Ile Phe Pro Pro Ser Asp Glu Gln Leu Lys Ser Gly
        275                 280                 285

Thr Ala Ser Val Val Cys Leu Leu Asn Asn Phe Tyr Pro Arg Glu Ala
    290                 295                 300

Lys Val Gln Trp Lys Val Asp Asn Ala Leu Gln Ser Gly Asn Ser Gln
305                 310                 315                 320

Glu Ser Val Thr Glu Gln Asp Ser Lys Asp Ser Thr Tyr Ser Leu Ser
                325                 330                 335

Ser Thr Leu Thr Leu Ser Lys Ala Asp Tyr Glu Lys His Lys Val Tyr
            340                 345                 350

Ala Cys Glu Val Thr His Gln Gly Leu Ser Ser Pro Val Thr Lys Ser
        355                 360                 365

Phe Asn Arg Gly Glu Cys
    370
```

```
<210> SEQ ID NO 43
<211> LENGTH: 56
<212> TYPE: DNA
<213> ORGANISM: Artificial Sequence
<220> FEATURE:
<223> OTHER INFORMATION: oligonucleotide primer ZC40915

<400> SEQUENCE: 43

acaggtgtcc agggaattca tataggccgg ccaccatgga tgcaatgaag agaggg         56


<210> SEQ ID NO 44
<211> LENGTH: 42
<212> TYPE: DNA
<213> ORGANISM: Artificial Sequence
<220> FEATURE:
<223> OTHER INFORMATION: oligonucleotide primer ZC44745

<400> SEQUENCE: 44

agatttgggc tcactagtcg aacccgaacc cgaaccggat cc                        42


<210> SEQ ID NO 45
<211> LENGTH: 42
<212> TYPE: DNA
<213> ORGANISM: Artificial Sequence
<220> FEATURE:
<223> OTHER INFORMATION: oligonucleotide primer ZC44744

<400> SEQUENCE: 45
```

-continued

```
ggatccggtt cgggttcggg ttcgactagt gagcccaaat ct                        42


<210> SEQ ID NO 46
<211> LENGTH: 1236
<212> TYPE: DNA
<213> ORGANISM: Artificial Sequence
<220> FEATURE:
<223> OTHER INFORMATION: DNA encoding fusion protein
<220> FEATURE:
<221> NAME/KEY: CDS
<222> LOCATION: (1)...(1236)

<400> SEQUENCE: 46

atg gat gca atg aag aga ggg ctc tgc tgt gtg ctg ctg ctg tgt ggc       48
Met Asp Ala Met Lys Arg Gly Leu Cys Cys Val Leu Leu Leu Cys Gly
 1               5                  10                  15

gcc gtc ttc gtt tcg ctc agc cag gaa atc cat gcc gag ttg aga cgc       96
Ala Val Phe Val Ser Leu Ser Gln Glu Ile His Ala Glu Leu Arg Arg
            20                  25                  30

ttc cgt aga ctg aac acg aca att ctg acg ccc aat ggg aat gaa gac      144
Phe Arg Arg Leu Asn Thr Thr Ile Leu Thr Pro Asn Gly Asn Glu Asp
        35                  40                  45

acc aca gct gat ttc ttc ctg acc act atg ccc act gac tcc ctc agt      192
Thr Thr Ala Asp Phe Phe Leu Thr Thr Met Pro Thr Asp Ser Leu Ser
    50                  55                  60

gtt tcc act ctg ccc ctc cca gag gtt cag tgt ttt gtg ttc aat gtc      240
Val Ser Thr Leu Pro Leu Pro Glu Val Gln Cys Phe Val Phe Asn Val
 65                  70                  75                  80

gag tac atg aat tgc act tgg aac agc agc tct gag ccc cag cct acc      288
Glu Tyr Met Asn Cys Thr Trp Asn Ser Ser Ser Glu Pro Gln Pro Thr
                85                  90                  95

aac ctc act ctg cat tat tgg tac aag aac tcg gat aat gat aaa gtc      336
Asn Leu Thr Leu His Tyr Trp Tyr Lys Asn Ser Asp Asn Asp Lys Val
            100                 105                 110

cag aag tgc agc cac tat cta ttc tct gaa gaa atc act tct ggc tgt      384
Gln Lys Cys Ser His Tyr Leu Phe Ser Glu Glu Ile Thr Ser Gly Cys
        115                 120                 125

cag ttg caa aaa aag gag atc cac ctc tac caa aca ttt gtt gtt cag      432
Gln Leu Gln Lys Lys Glu Ile His Leu Tyr Gln Thr Phe Val Val Gln
    130                 135                 140

ctc cag gac cca cgg gaa ccc agg aga cag gcc aca cag atg cta aaa      480
Leu Gln Asp Pro Arg Glu Pro Arg Arg Gln Ala Thr Gln Met Leu Lys
145                 150                 155                 160

ctg cag aat ctg gtg atc ccc tgg gct cca gag aac cta aca ctt cac      528
Leu Gln Asn Leu Val Ile Pro Trp Ala Pro Glu Asn Leu Thr Leu His
                165                 170                 175

aaa ctg agt gaa tcc cag cta gaa ctg aac tgg aac aac aga ttc ttg      576
Lys Leu Ser Glu Ser Gln Leu Glu Leu Asn Trp Asn Asn Arg Phe Leu
            180                 185                 190

aac cac tgt ttg gag cac ttg gtg cag tac cgg act gac tgg gac cac      624
Asn His Cys Leu Glu His Leu Val Gln Tyr Arg Thr Asp Trp Asp His
        195                 200                 205

agc tgg act gaa caa tca gtg gat tat aga cat aag ttc tcc ttg cct      672
Ser Trp Thr Glu Gln Ser Val Asp Tyr Arg His Lys Phe Ser Leu Pro
    210                 215                 220

agt gtg gat ggg cag aaa cgc tac acg ttt cgt gtt cgg agc cgc ttt      720
Ser Val Asp Gly Gln Lys Arg Tyr Thr Phe Arg Val Arg Ser Arg Phe
225                 230                 235                 240

aac cca ctc tgt gga agt gct cag cat tgg agt gaa tgg agc cac cca      768
Asn Pro Leu Cys Gly Ser Ala Gln His Trp Ser Glu Trp Ser His Pro
                245                 250                 255
```

-continued

```
atc cac tgg ggg agc aat act tca aaa gag aat gga tcc ggt tcg ggt      816
Ile His Trp Gly Ser Asn Thr Ser Lys Glu Asn Gly Ser Gly Ser Gly
            260                 265                 270

tcg ggt tcg act agt gag ccc aaa tct agc gac aaa act cac aca tgc      864
Ser Gly Ser Thr Ser Glu Pro Lys Ser Ser Asp Lys Thr His Thr Cys
        275                 280                 285

cca ccg tgc cca ggt gga gga tcc ggc ggt gga tca ctg gtt ccg cgt      912
Pro Pro Cys Pro Gly Gly Gly Ser Gly Gly Gly Ser Leu Val Pro Arg
    290                 295                 300

cga act gtg gct gca cca tct gtc ttc atc ttc ccg cca tct gat gag      960
Arg Thr Val Ala Ala Pro Ser Val Phe Ile Phe Pro Pro Ser Asp Glu
305                 310                 315                 320

cag ttg aaa tct ggt acc gcc tct gtt gtg tgc ctg ctg aat aac ttc     1008
Gln Leu Lys Ser Gly Thr Ala Ser Val Val Cys Leu Leu Asn Asn Phe
                325                 330                 335

tat ccc aga gag gcc aaa gta cag tgg aag gtg gat aac gcc ctc caa     1056
Tyr Pro Arg Glu Ala Lys Val Gln Trp Lys Val Asp Asn Ala Leu Gln
            340                 345                 350

tcg ggt aac tcc cag gag agt gtc aca gag cag gac agc aag gac agc     1104
Ser Gly Asn Ser Gln Glu Ser Val Thr Glu Gln Asp Ser Lys Asp Ser
        355                 360                 365

acc tac agc ctc agc agc acc ctg acg ctg agc aaa gca gac tac gag     1152
Thr Tyr Ser Leu Ser Ser Thr Leu Thr Leu Ser Lys Ala Asp Tyr Glu
    370                 375                 380

aaa cac aaa gtc tac gcc tgc gaa gtc acc cat cag ggc ctg agc tcg     1200
Lys His Lys Val Tyr Ala Cys Glu Val Thr His Gln Gly Leu Ser Ser
385                 390                 395                 400

ccc gtc aca aag agc ttc aac agg gga gag tgt taa                     1236
Pro Val Thr Lys Ser Phe Asn Arg Gly Glu Cys  *
                405                 410


<210> SEQ ID NO 47
<211> LENGTH: 411
<212> TYPE: PRT
<213> ORGANISM: Artificial Sequence
<220> FEATURE:
<223> OTHER INFORMATION: fusion protein

<400> SEQUENCE: 47

Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
            20                  25                  30

Phe Arg Arg Leu Asn Thr Thr Ile Leu Thr Pro Asn Gly Asn Glu Asp
        35                  40                  45

Thr Thr Ala Asp Phe Phe Leu Thr Thr Met Pro Thr Asp Ser Leu Ser
    50                  55                  60

Val Ser Thr Leu Pro Leu Pro Glu Val Gln Cys Phe Val Phe Asn Val
65                  70                  75                  80

Glu Tyr Met Asn Cys Thr Trp Asn Ser Ser Ser Glu Pro Gln Pro Thr
                85                  90                  95

Asn Leu Thr Leu His Tyr Trp Tyr Lys Asn Ser Asp Asn Asp Lys Val
            100                 105                 110

Gln Lys Cys Ser His Tyr Leu Phe Ser Glu Glu Ile Thr Ser Gly Cys
        115                 120                 125

Gln Leu Gln Lys Lys Glu Ile His Leu Tyr Gln Thr Phe Val Val Gln
    130                 135                 140

Leu Gln Asp Pro Arg Glu Pro Arg Arg Gln Ala Thr Gln Met Leu Lys
145                 150                 155                 160
```

```
Leu Gln Asn Leu Val Ile Pro Trp Ala Pro Glu Asn Leu Thr Leu His
                165                 170                 175

Lys Leu Ser Glu Ser Gln Leu Glu Leu Asn Trp Asn Asn Arg Phe Leu
            180                 185                 190

Asn His Cys Leu Glu His Leu Val Gln Tyr Arg Thr Asp Trp Asp His
        195                 200                 205

Ser Trp Thr Glu Gln Ser Val Asp Tyr Arg His Lys Phe Ser Leu Pro
    210                 215                 220

Ser Val Asp Gly Gln Lys Arg Tyr Thr Phe Arg Val Arg Ser Arg Phe
225                 230                 235                 240

Asn Pro Leu Cys Gly Ser Ala Gln His Trp Ser Glu Trp Ser His Pro
                245                 250                 255

Ile His Trp Gly Ser Asn Thr Ser Lys Glu Asn Gly Ser Gly Ser Gly
            260                 265                 270

Ser Gly Ser Thr Ser Glu Pro Lys Ser Ser Asp Lys Thr His Thr Cys
        275                 280                 285

Pro Pro Cys Pro Gly Gly Gly Ser Gly Gly Gly Ser Leu Val Pro Arg
    290                 295                 300

Arg Thr Val Ala Ala Pro Ser Val Phe Ile Phe Pro Pro Ser Asp Glu
305                 310                 315                 320

Gln Leu Lys Ser Gly Thr Ala Ser Val Val Cys Leu Leu Asn Asn Phe
                325                 330                 335

Tyr Pro Arg Glu Ala Lys Val Gln Trp Lys Val Asp Asn Ala Leu Gln
            340                 345                 350

Ser Gly Asn Ser Gln Glu Ser Val Thr Glu Gln Asp Ser Lys Asp Ser
        355                 360                 365

Thr Tyr Ser Leu Ser Ser Thr Leu Thr Leu Ser Lys Ala Asp Tyr Glu
    370                 375                 380

Lys His Lys Val Tyr Ala Cys Glu Val Thr His Gln Gly Leu Ser Ser
385                 390                 395                 400

Pro Val Thr Lys Ser Phe Asn Arg Gly Glu Cys
                405                 410


<210> SEQ ID NO 48
<211> LENGTH: 103
<212> TYPE: PRT
<213> ORGANISM: Homo sapiens

<400> SEQUENCE: 48

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100
```

-continued

```
<210> SEQ ID NO 49
<211> LENGTH: 104
<212> TYPE: PRT
<213> ORGANISM: Homo sapiens

<400> SEQUENCE: 49

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Ala Glu Arg Lys Cys Cys
            100


<210> SEQ ID NO 50
<211> LENGTH: 103
<212> TYPE: PRT
<213> ORGANISM: Homo sapiens

<400> SEQUENCE: 50

Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro
            100


<210> SEQ ID NO 51
<211> LENGTH: 103
<212> TYPE: PRT
<213> ORGANISM: Homo sapiens

<400> SEQUENCE: 51

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80
```

```
Tyr Thr Cys Asn Val Asp His Lys Pro Ser Asn Thr Lys Val Asp Lys
                85                  90                  95

Arg Val Glu Ser Lys Tyr Gly
            100


<210> SEQ ID NO 52
<211> LENGTH: 101
<212> TYPE: PRT
<213> ORGANISM: Homo sapiens

<400> SEQUENCE: 52

Ala Ser Pro Thr Ser Pro Lys Val Phe Pro Leu Ser Leu Cys Ser Thr
 1               5                  10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys
            100


<210> SEQ ID NO 53
<211> LENGTH: 101
<212> TYPE: PRT
<213> ORGANISM: Homo sapiens

<400> SEQUENCE: 53

Ala Ser Pro Thr Ser Pro Lys Val Phe Pro Leu Ser Leu Asp Ser Thr
 1               5                  10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys
            100


<210> SEQ ID NO 54
<211> LENGTH: 104
<212> TYPE: PRT
<213> ORGANISM: Homo sapiens

<400> SEQUENCE: 54

Ala Pro Thr Lys Ala Pro Asp Val Phe Pro Ile Ile Ser Gly Cys Arg
 1               5                  10                  15

His Pro Lys Asp Asn Ser Pro Val Val Leu Ala Cys Leu Ile Thr Gly
            20                  25                  30
```

-continued

```
Tyr His Pro Thr Ser Val Thr Val Thr Trp Tyr Met Gly Thr Gln Ser
        35                  40                  45

Gln Pro Gln Arg Thr Phe Pro Glu Ile Gln Arg Arg Asp Ser Tyr Tyr
    50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro
            100


<210> SEQ ID NO 55
<211> LENGTH: 105
<212> TYPE: PRT
<213> ORGANISM: Homo sapiens

<400> SEQUENCE: 55

Ala Ser Thr Gln Ser Pro Ser Val Phe Pro Leu Thr Arg Cys Cys Lys
 1               5                  10                  15

Asn Ile Pro Ser Asn Ala Thr Ser Val Thr Leu Gly Cys Leu Ala Thr
            20                  25                  30

Gly Tyr Phe Pro Glu Pro Val Met Val Thr Trp Asp Thr Gly Ser Leu
        35                  40                  45

Asn Gly Thr Thr Met Thr Leu Pro Ala Thr Thr Leu Thr Leu Ser Gly
    50                  55                  60

His Tyr Ala Thr Ile Ser Leu Leu Thr Val Ser Gly Ala Trp Ala Lys
65                  70                  75                  80

Gln Met Phe Thr Cys Arg Val Ala His Thr Pro Ser Ser Thr Asp Trp
                85                  90                  95

Val Asp Asn Lys Thr Phe Ser Val Cys
            100                 105


<210> SEQ ID NO 56
<211> LENGTH: 105
<212> TYPE: PRT
<213> ORGANISM: Homo sapiens

<400> SEQUENCE: 56

Gly Ser Ala Ser Ala Pro Thr Leu Phe Pro Leu Val Ser Cys Glu Asn
 1               5                  10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val
            100                 105


<210> SEQ ID NO 57
<211> LENGTH: 103
<212> TYPE: PRT
<213> ORGANISM: Artificial Sequence
<220> FEATURE:
```

-continued

<223> OTHER INFORMATION: Consensus CH1 domain

<400> SEQUENCE: 57

```
Ala Ser Thr Lys Gly Pro Ser Val Phe Pro Leu Ala Pro Cys Ser Arg
 1               5                  10                  15

Ser Thr Ser Gly Gly Thr Val Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Asp Val Thr Val Lys Val Cys
            100
```

<210> SEQ ID NO 58
<211> LENGTH: 91
<212> TYPE: PRT
<213> ORGANISM: Mus musculus

<400> SEQUENCE: 58

```
Ser Ile Arg Asn Pro Gln Leu Tyr Pro Leu Lys Pro Cys Lys Gly Thr
 1               5                  10                  15

Ala Ser Met Thr Leu Gly Cys Leu Val Lys Asp Tyr Phe Pro Asn Pro
            20                  25                  30

Val Thr Val Thr Trp Tyr Ser Asp Ser Leu Asn Met Ser Thr Val Asn
        35                  40                  45

Phe Pro Ala Leu Gly Ser Glu Leu Lys Val Thr Thr Ser Gln Val Thr
    50                  55                  60

Ser Trp Gly Lys Ser Ala Lys Asn Phe Thr Cys His Val Thr His Pro
65                  70                  75                  80

Pro Ser Phe Asn Glu Ser Arg Thr Ile Leu Gly
                85                  90
```

<210> SEQ ID NO 59
<211> LENGTH: 97
<212> TYPE: PRT
<213> ORGANISM: Mus musculus

<400> SEQUENCE: 59

```
Ala Lys Thr Thr Ala Pro Ser Val Tyr Pro Leu Ala Pro Val Cys Gly
 1               5                  10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile
```

<210> SEQ ID NO 60
<211> LENGTH: 96
<212> TYPE: PRT
<213> ORGANISM: Mus musculus

<400> SEQUENCE: 60

```
Thr Thr Thr Ala Pro Ser Val Tyr Pro Leu Val Pro Gly Cys Ser Asp
 1               5                  10                  15

Thr Ser Gly Ser Ser Val Thr Leu Gly Cys Leu Val Lys Gly Tyr Phe
            20                  25                  30

Pro Glu Pro Val Thr Val Lys Trp Asn Tyr Gly Ala Leu Ser Ser Gly
        35                  40                  45

Val Arg Thr Val Ser Ser Val Leu Gln Ser Gly Phe Tyr Ser Leu Ser
    50                  55                  60

Ser Leu Val Thr Val Pro Ser Ser Thr Trp Pro Ser Gln Thr Val Ile
65                  70                  75                  80

Cys Asn Val Ala His Pro Ala Ser Lys Thr Glu Leu Ile Lys Arg Ile
                85                  90                  95
```

<210> SEQ ID NO 61
<211> LENGTH: 107
<212> TYPE: PRT
<213> ORGANISM: Homo sapiens

<400> SEQUENCE: 61

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 62
<211> LENGTH: 105
<212> TYPE: PRT
<213> ORGANISM: Homo sapiens

<400> SEQUENCE: 62

```
Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
```

-continued

```
                85                  90                  95

Lys Thr Val Ala Pro Thr Glu Cys Ser
            100                 105


<210> SEQ ID NO 63
<211> LENGTH: 108
<212> TYPE: PRT
<213> ORGANISM: Artificial Sequence
<220> FEATURE:
<223> OTHER INFORMATION: Consensus light chain constant domain

<400> SEQUENCE: 63

Gln Thr Val Ala Ala Pro Ser Val Thr Leu Phe Pro Pro Ser Ser Glu
 1               5                  10                  15

Glu Leu Gln Ala Gly Thr Ala Ser Val Val Cys Leu Leu Ser Asp Phe
            20                  25                  30

Tyr Pro Gly Ala Ala Thr Val Ala Trp Lys Ala Asp Ser Ala Leu Val
        35                  40                  45

Ser Gly Gly Val Glu Thr Ser Val Thr Ser Gln Asp Ser Asn Asp Ser
    50                  55                  60

Thr Tyr Ala Ala Ser Ser Thr Leu Ser Leu Ser Lys Ala Asp Tyr Glu
65                  70                  75                  80

Ser His Lys Val Tyr Ala Cys Glu Val Thr His Glu Gly Leu Ser Ser
                85                  90                  95

Thr Val Thr Lys Ser Val Ala Arg Gly Glu Cys Ser
            100                 105
```